US012699086B2

(12) United States Patent
Medkova et al.

(10) Patent No.:  US 12,699,086 B2
(45) Date of Patent:  Aug. 4, 2026

(54) MODIFIED ELISA WITH HEMOGLOBIN CORRECTION APPARATUS AND METHODS THEREOF

(71) Applicant: NOVA BIOMEDICAL CORPORATION, Waltham, MA (US)

(72) Inventors: Martina Medkova, Winchester, MA (US); Daniel King, Northborough, MA (US); Jeff Chien, Wellesley, MA (US)

(73) Assignee: NOVA BIOMEDICAL CORPORATION, Waltham, MA (US)

( * ) Notice: Subject to any disclaimer, the term of this patent is extended or adjusted under 35 U.S.C. 154(b) by 511 days.

(21) Appl. No.: 18/034,448

(22) PCT Filed: Nov. 23, 2020

(86) PCT No.: PCT/US2020/061721
§ 371 (c)(1),
(2) Date: Apr. 28, 2023

(87) PCT Pub. No.: WO2022/108600
PCT Pub. Date: May 27, 2022

(65) Prior Publication Data
US 2023/0400457 A1     Dec. 14, 2023

(51) Int. Cl.
*G01N 33/53*       (2006.01)
*B01L 3/00*        (2006.01)
(Continued)

(52) U.S. Cl.
CPC ........ *G01N 33/5304* (2013.01); *B01L 3/0275* (2013.01); *B01L 3/502715* (2013.01);
(Continued)

(58) Field of Classification Search
CPC ......... G01N 33/5304; G01N 33/54386; G01N 2035/103; G01N 33/54366; B01L 3/0275;
(Continued)

(56) References Cited

U.S. PATENT DOCUMENTS 7,632,462 B2    12/2009  Holtlund et al.
9,701,957 B2 *   7/2017  Wilson ................. C12Q 1/6813
(Continued)

FOREIGN PATENT DOCUMENTS

JP       2004531725 A    10/2004
JP       2010540971 A    12/2010
(Continued)

OTHER PUBLICATIONS

Sharafeldin et al., "Accessible Telemedicine Diagnostics with ELISA in a 3D Printed Pipette Tip", ACS Publications, Analytical Chemistry, vol. 91, Issue 11, 2019, 15 pages.
Scheffer et al., "Expression of the vascular endothelial cell protein C receptor in epithelial tumour cells", European Journal of Cancer, 2002, vol. 38, Issue 11, pp. 1535-1542, 6 pages.

*Primary Examiner* — Christopher L Chin
(74) *Attorney, Agent, or Firm* — Hayes Soloway PC

(57)        ABSTRACT
A disposable bioassay diagnostic cartridge for performing enzyme-linked immunosorbent assay for a single patient in whole blood and plasma where the cartridge has a plurality of wells. The cartridge includes a pipette tip with internal sidewalls disposed in one well of the plurality of wells, the internal sidewalls being pretreated and coated with antibodies, a reagent mixture disposed in another well of the plurality of wells, the reagent mixture comprising at least one reagent selected from the group consisting of pH stabilizer, ionic catalyst control agent, ionic intracellular inhibitory control agent, detergent, negative control agent, chelating agent, and biocide preservative, antibody, and conjugate stabilizing agent. At least a chromogenic substrate and visualizing reagent disposed in an integrated cuvette of the plurality of wells. It also includes the detection of the hemoglobin amount in the blood sample so a correction for plasma amount in a sample can be performed.

18 Claims, 13 Drawing Sheets

(51) Int. Cl.
    *B01L 3/02*          (2006.01)
    *G01N 33/543*     (2006.01)

(52) U.S. Cl.
    CPC .. *G01N 33/54386* (2013.01); *B01L 2200/025*
           (2013.01); *B01L 2200/04* (2013.01); *B01L*
           *2200/16* (2013.01); *B01L 2300/027* (2013.01)

(58) Field of Classification Search
    CPC .. B01L 3/502715; B01L 3/021; B01L 3/5085;
           B01L 3/527; B01L 3/52; B01L
           2300/0829; B01L 9/54; B01L 9/543;
           B01L 2200/025; B01L 2200/04; B01L
           2200/16; B01L 2300/027; B01L
           2300/046; B01L 2300/06
    USPC .... 422/402–404, 407, 408, 419, 82.05, 501,
           422/524, 526, 551–554, 564; 427/2.11;
           435/7.5, 7.9, 7.92, 288.4, 288.7, 968;
           436/164, 172, 176, 518, 805, 809
    See application file for complete search history.

(56)            References Cited

U.S. PATENT DOCUMENTS

| | | |
|---|---|---|
| 2019/0038196 A1 | 2/2019 | Young et al. |
| 2020/0057085 A1 | 2/2020 | Wasson et al. |

FOREIGN PATENT DOCUMENTS

| | | |
|---|---|---|
| KR | 20220082858 A | 6/2022 |
| WO | 2005000470 A1 | 1/2005 |
| WO | 2006090154 A1 | 8/2006 |
| WO | 2014198836 A1 | 12/2014 |
| WO | 2018234682 A1 | 12/2018 |
| WO | 2019087176 | 5/2019 |
| WO | 2021076134 A1 | 4/2021 |

* cited by examiner

Figure 15: CRP dose-response
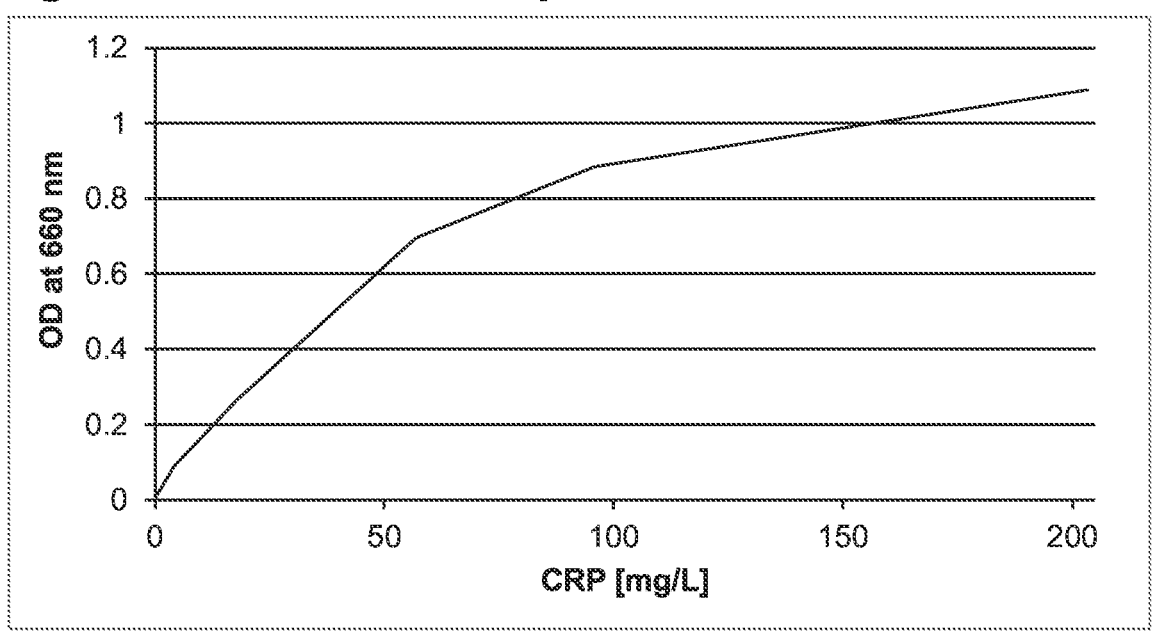
Figure 16: Cystatin dose-response
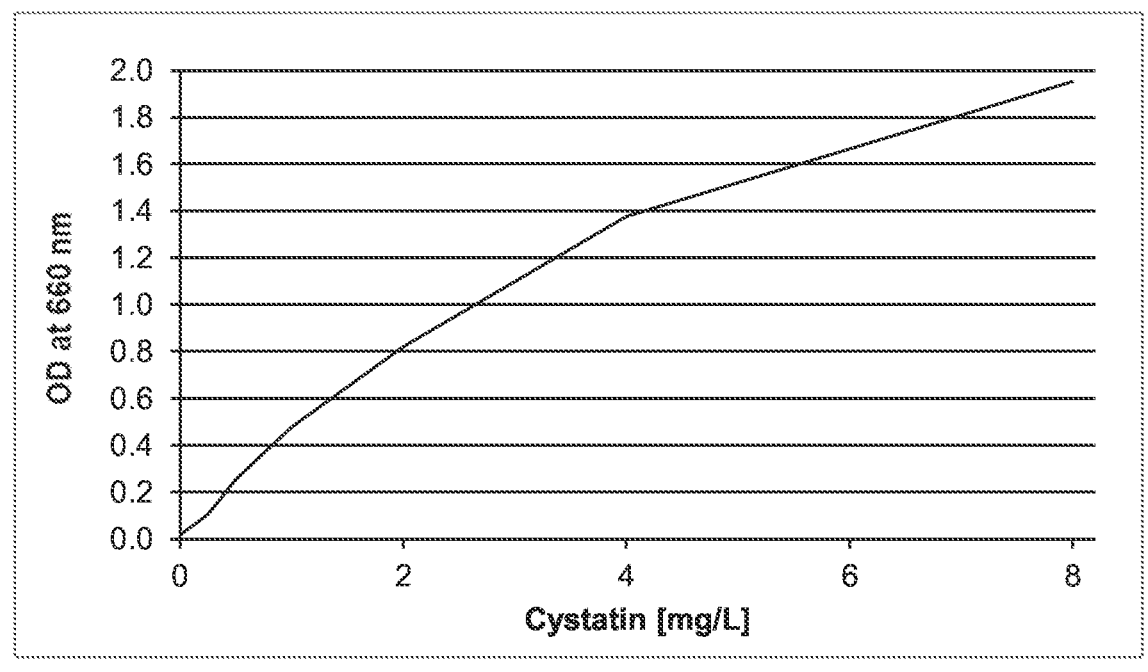

Figure 17: ALT dose-response
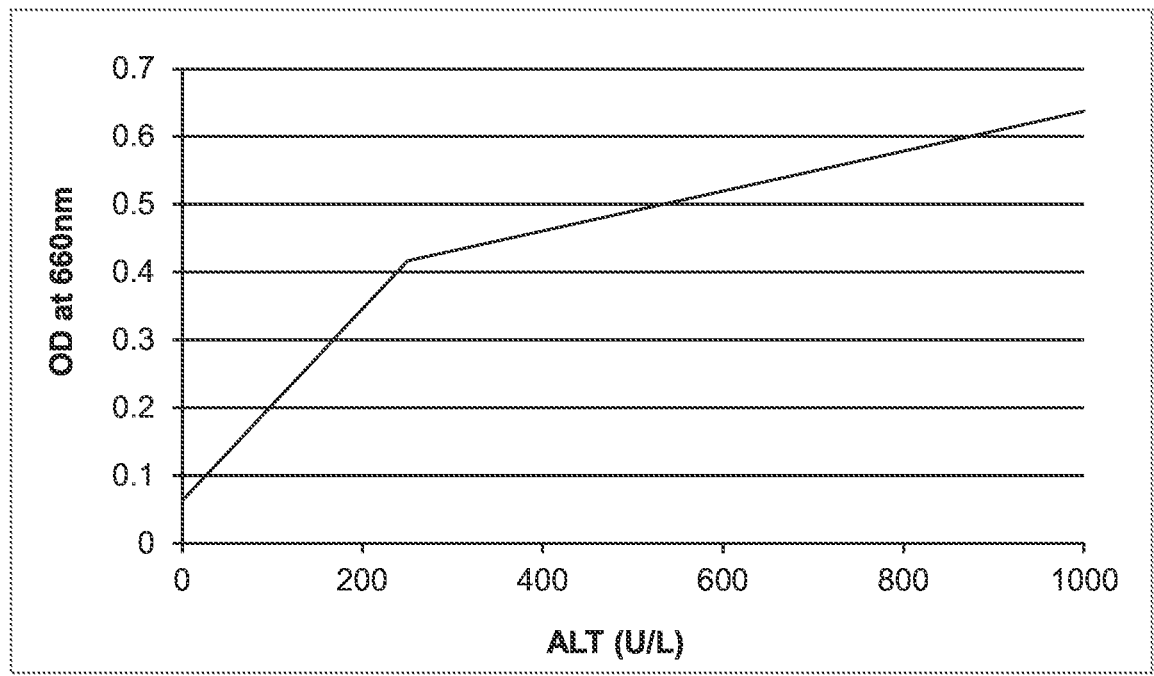
Figure 18: AST dose-response
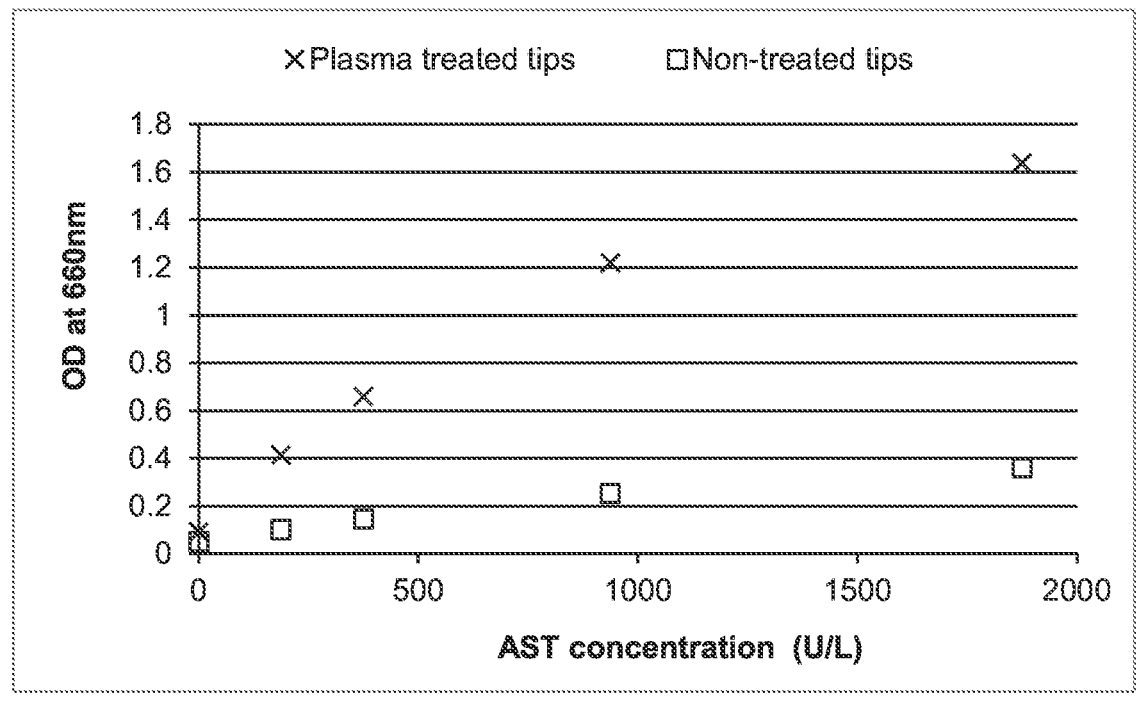

Figure 19: hs-CRP dose-response
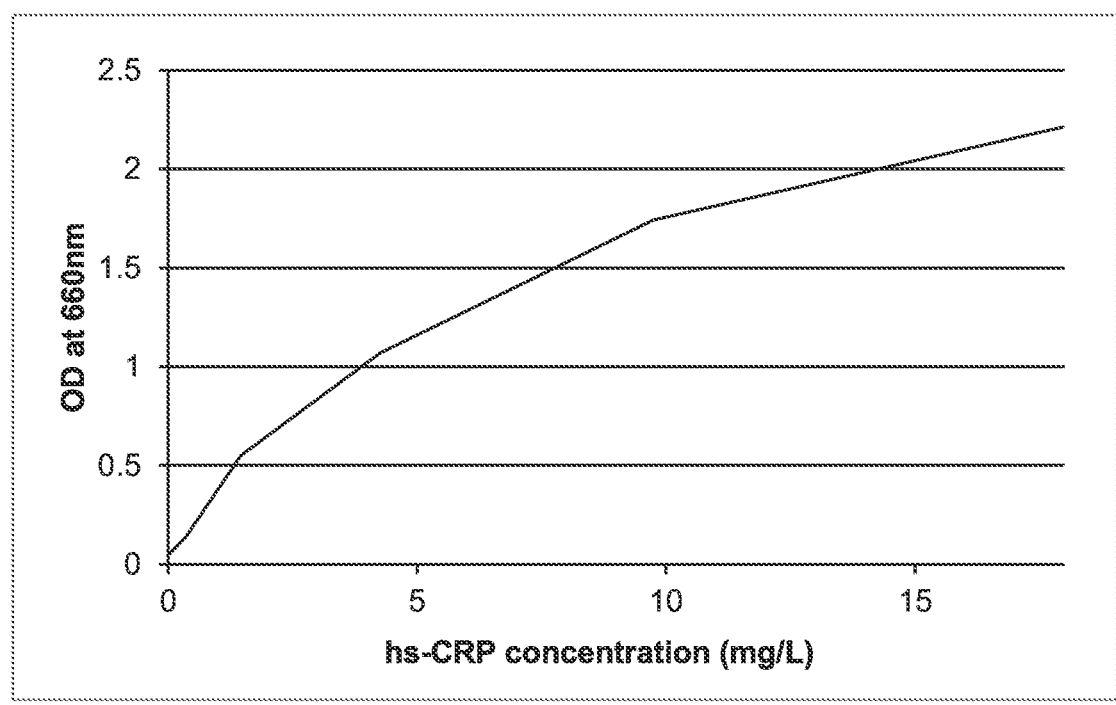
Figure 20: IGF-1 dose-response
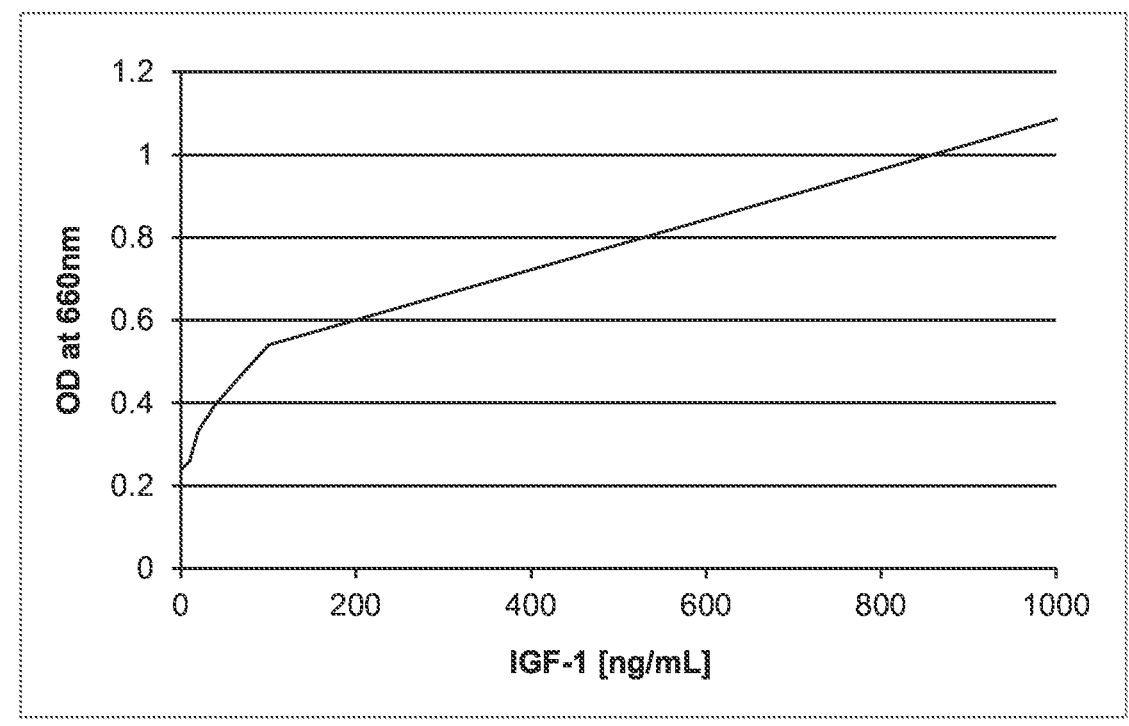

Figure 21: CRP Against HGB
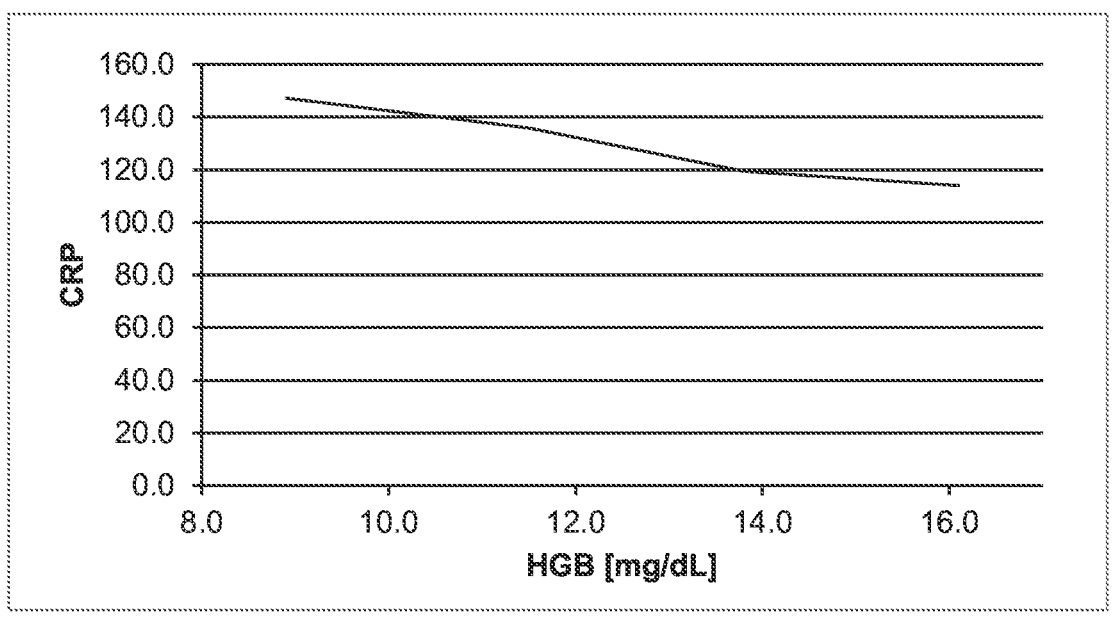
Figure 22: CRP Against HGB Corrected
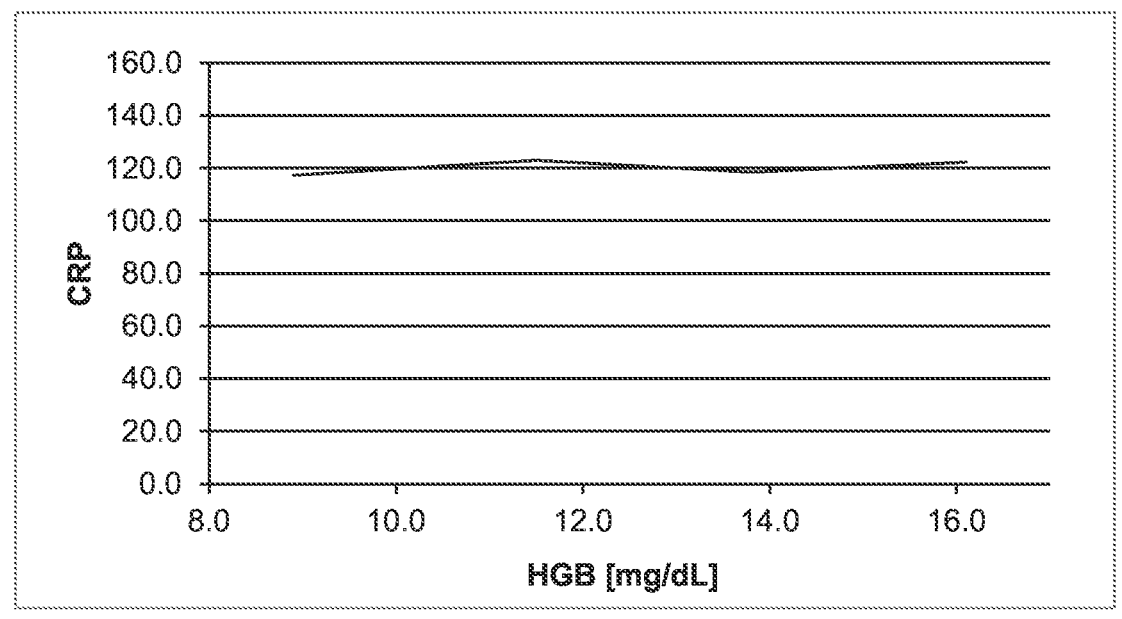

MODIFIED ELISA WITH HEMOGLOBIN CORRECTION APPARATUS AND METHODS THEREOF

CROSS-REFERENCE TO RELATED APPLICATIONS AND PRIORITY

This patent application claims priority from PCT/US2020/061721 filed Nov. 23, 2020, which is herein incorporated by reference in its entirety.

BACKGROUND OF THE INVENTION

1. Field of the Invention

The present invention relates generally to a method and apparatus for enzyme-linked immunosorbent assays.

2. Description of the Prior Art

Enzyme-linked immunosorbent assay (ELISA), is a biochemical technique used to detect and/or quantify an antibody or an antigen in a sample. Classical 2 step sandwich ELISA is based on an initial binding of an analyte to capture antibodies against the analyte followed by binding of labeled detector antibody to captured analyte. In one step sandwich ELISA, analyte binding to capture and detector antibodies is performed at the same time. Detector antibodies can be conjugated to enzymes such as horseradish peroxidase (HRP) or alkaline phosphatase (AP). Subsequent introduction of enzyme substrate to captured immune complexes results in color formation which can be measured optically or by other means. The rate and extent of color formation is proportional to concentration of antigen.

ELISA is typically performed in microtiter plate format and requires either complex instrumentation and/or highly skilled personnel. ELISA is also typically performed using 96-well or 384-well polystyrene plates and samples in solution. In addition to traditional ELISA kits which include only the capture antibody when the sample is added, other instant ELISA kits contain pre-treated plates holding capture antibody and lyophilized detection antibody, streptavidin-HRP, and sample diluent.

U.S. Pat. No. 9,011,772, titled Apparatus for And Method of Automated Processing Of Biological Samples, discloses a bioprocessing device, bioprocessing card, and fluidics cartridge for performing automated bioprocessing of a sample. The bioprocessing card may include a plurality of pipette tips; and at least one pump in fluid communication with the plurality of pipette tips. In some embodiments, the pumps and the pipette tips are in fluid communication through a processing channel which may be a microscale channel. Also provided therein is an automated bioprocessing device comprising at least one bioprocessing card; at least one fluidic cartridge; and an automated control system configured to control automated bioprocessing of a sample. Further provided herein are methods of use of the device, card, and cartridge.

U.S. Pat. No. 9,810,704, titled Systems and Methods for Multi-Analysis discloses systems and methods for sample processing. Specifically, disclosing a device may be provided, capable of receiving the sample, and performing one or more of a sample preparation, sample assay, and detection step. The device may be capable of performing multiple assays. The device may comprise one or more modules that may be capable of performing one or more of a sample preparation, sample assay, and detection step. The device may be capable of performing the steps using a small volume of sample.

SUMMARY OF THE INVENTION

Advantages and Differences of Invention Over Known Prior Art

The above-described parts of the prior art have not proven fully satisfactory for meeting all of the requirements of the industry.

A few of the advantages of the present inventive method of providing a modified-ELISA self-contained kit providing increased capabilities will now be discussed. One advantage of modifying the usual ELISA methodology includes increasing the functionality of an associated pipette tip. A further benefit is associated with increased washing resulting in reduced or eliminated cross-contamination. A further benefit of the present inventive method is that the enzyme-substrate reaction does not need to be stopped before testing. An additional benefit of the modified-ELISA of the present invention is a faster immunoassay which provides results in less than 15 minutes, more preferably in about 10-14 minutes, and in some embodiments in a range of 7-9 minutes.

Meeting the Objectives of the Present Invention

The present invention provides an enzyme-linked immunosorbent assay system having a movable element to which capture affinity reagents are bound. In one embodiment the capture affinity reagents are antibodies. In one embodiment the movable element is a pipette tip. In a further embodiment, the system employs a disposable cartridge with multiple wells capable of holding multiple distinct reagents. In this embodiment, dimensions of the wells are compatible with the above-mentioned movable element, so that the movable element can be inserted into the wells and aspirate, hold, dispense and move liquids around the cartridge.

The system may employ a sample collection device able to deliver specified volume of sample into the cartridge. The preferred system may also employ an instrument able to engage a movable element and accurately aspirate, dispense, transfer and mix various biomaterials and detect the presence of different analytes optically.

In a preferred embodiment, movable elements such as pipette tip and a reagent cartridge can be made of various materials such as polystyrene (PS), polypropylene (PP), polyethylene PE), polymethyl methacrylate (PMMA), polydimethylsiloxane (PDMS), polycarbonate (PC), cyclic olefin copolymer such as TOP AS®, cyclo-olefin polymer such as Zeonor®, and Zeonex®, cellulose and its derivatives, silicon and its derivatives, glass, quartz, or metals.

In a preferred embodiment, movable element such as pipette tip can be coated with a protein such as antibody, antibody fragment, a recombinant protein, protein A, protein G, protein A/G, streptavidin, or recombinant proteins or fragments thereof, nucleic acid, polysaccharide, glycoprotein, peptidoglycans, molecular imprinted polymer or aptamer molecule. An antibody is the preferred affinity agent. Immobilization can be achieved by nonspecific adsorption or by covalent conjugation.

In a preferred embodiment, cartridge wells are pre-filled with reagents such as sample lysis buffer, wash buffer, detector antibody conjugate and enzyme substrate. In a preferred embodiment, detector antibodies can be conjugated to enzymes such as horseradish peroxidase (HRP) or alkaline phosphatase (AP).

Another objective is to provide a system and method by which multiple types of ELISA may be performed. Thus, according to the present inventive methods, both 1-step and 2-step ELISA may be performed.

The present invention achieves these and other objectives by providing a point of care disposable bioassay diagnostic cartridge for performing enzyme-linked immunosorbent assays. The disposable cartridge may have multiple wells, a first well may hold a pipette tip with internal sidewalls which are pretreated and coated with specific antibodies. A second well of the cartridge may have at least one reagent mixture with at least one reagent being a pH stabilizer, ionic catalyst control agent, ionic intracellular inhibitory control agent, detergent, negative control agent, chelating agent, and biocide preservative, antibody, and conjugate stabilizing agent. The antibody may be one or more of anti-c-reactive protein antibodies, anti-cystatin-c antibodies, anti-IGF-1 antibodies, anti-alanine aminotransferase antibodies, and anti-aspartate aminotransferase antibodies. A third well may hold a reagent mixture with at least one of a chromogenic substrate and visualizing reagent.

The present invention also meets these objectives by providing an enzyme-linked immunosorbent bioassay diagnostic kit having a fingerstick device and a unitary self-contained disposable diagnostic cartridge. The cartridge may have a pipette-tip and bioassay components which are contained within the cartridge. The cartridge may also have an integral optical cuvette. The cartridge may also have an identifier along an outer surface for user ease.

The pipette-tip within the cartridge has internal sidewalls which are coated with an antibody, and a least a portion within an internal chamber of the pipette-tip which remains open and accessible to the internal sidewalls. That is, the coated pipette-tip is not entirely filled, but remains fillable.

The bioassay components within the cartridge have at least one reactive or nonreactive reagent: pH stabilizer, ionic catalyst control agent, ionic intracellular inhibitory control agent, detergent, negative control agent, chelating agent, and biocide preservative, an antibody, conjugate stabilizing agent, a chromogenic substrate, and visualizing reagent.

The pipette-tips of the present invention may have internal walls coated with varying amounts of antibodies. Similarly, the cartridge wells of the present invention may have varying amount of bioassay components. Examples of modified-ELISA performed in accordance with the present invention are provided herein with specific amounts. However, it is to be understood that these amounts may vary dependent upon the size of the cartridge and tip employed without deviating from the spirit of the invention. The present invention generally employs antibodies and chromogenic substrate in similar amounts.

For example, an approximate correlation of 1:1 of antibodies to chromogenic substrate is present in most embodiments. When 40 ul to 60 ul of antibodies are utilized, there is generally present a range of 40 ul to 60 ul of chromogenic substrate is also utilized. When around 90 ul to 110 ul of antibodies are utilized, there is generally present a range of 90 ul to 110 ul of chromogenic substrate is also utilized. When an amount in a range of 300 ul to 320 ul of antibodies is used, there is also generally present about of 300 ul to 320 ul of chromogenic substrate.

The present inventive concept further meets the current objectives by providing a new method for preparing a cartridge for performing enzyme-linked immunosorbent assays. The method having steps of (1) pretreating a pipette tip by coating an internal surface of the pipette tip; (2) providing a first coating along the internal surface of the pipette tip with an affinity agent; (3) providing a second coating on top of the first coating along the internal surface of the pipette tip with a blocking solution; (4) providing a third coating on top of the second coating along the internal surface of the pipette tip with an activity preservative; (5) reducing washing time by facilitating direct pipetting with at least one reagent mixture being chosen from a group consisting of pH stabilizer, ionic catalyst control agent, ionic intracellular inhibitory control agent, detergent, negative control agent, chelating agent, and biocide preservative, an antibody, and conjugate stabilizing agent; and (6) providing one well within the cartridge for directly reacting with a chromogenic substrate and visualizing reagent.

This method may also include selecting the affinity agent from a group consisting of antibody, antibody fragment, recombinant protein, protein A, protein G, protein A/G, streptavidin, recombinant protein fragment, nucleic acid, polysaccharide, glycoprotein, peptidoglycans, molecular imprinted polymer, and aptamer molecule.

This method may also include selecting a coating buffer from a group consisting of a carbonate/bicarbonate buffer, sucrose buffer, phosphate buffered saline (PBS), and tris (hydroxymethyl)aminomethane saline.

Providing the first coating along the internal surface of the pipette tip with the affinity agent may also be further defined by selecting the affinity agent; selecting a coating buffer; preparing an antibody solution by mixing the selected antibody and the selected coating buffer; filling the pipette tips with the mixed antibody solution; and incubating the pipette tips at a first temperature for a first time.

Providing the second coating on top of the first coating along the internal surface of the pipette tip with the blocking solution, may also be further defined by selecting the blocking solution; filling the pipette tips with the blocking solution; and incubating the pipette tips at a second temperature for a second time.

Providing the third coating on top of the second coating along the internal surface of the pipette tip with the activity preservative, may also be further defined by selecting the activity preservative; filling the pipette tips with the activity preservative; and incubating the pipette tips at a third temperature for a third time.

BRIEF DESCRIPTION OF THE DRAWINGS

FIG. 15 a graph illustrating the results of first embodiments employing a dose response of CRP by measuring optical density at 660 nm against CRP (mg/L).

FIG. 16 is a graph illustrating the results of further embodiments employing a dose response of Cystatin by measuring optical density at 660 nm against Cystatin (mg/L).

FIG. 17 is a graph illustrating the results of further embodiments employing a dose response of ALT by measuring optical density at 660 nm against ALT concentration in (U/L).

FIG. 18 is a graph illustrating the results of further embodiments employing a dose response of AST-Nontreated by measuring optical density at 660 nm against AST concentration in (U/L).

FIG. 19 is a graph illustrating the results of further embodiments employing a dose response of hs-CRP by measuring optical density at 660 nm against hs-CRP concentration in (mg/L).

FIG. 20 is a graph illustrating the results of further embodiments employing a dose response of IGF-1 by measuring optical density at 660 nm against IGF-1 concentration in (ng/mL).

FIG. 21 is a graph illustrating the results of HGB effect on Normal CRP optical density readings.

FIG. 22 is a graph illustrating the corrected normal CRP optical density readings to account for HGB effect.

DETAILED DESCRIPTION OF THE INVENTION

The preferred embodiments of the present invention are discussed in reference to FIGS. 1-22. As discussed above, the present invention provides a process, methodology, system, and apparatus relating to a method and apparatus for a modified ELISA with hemoglobin correction.

All-Inclusive Cartridge Kit

Figure 1:
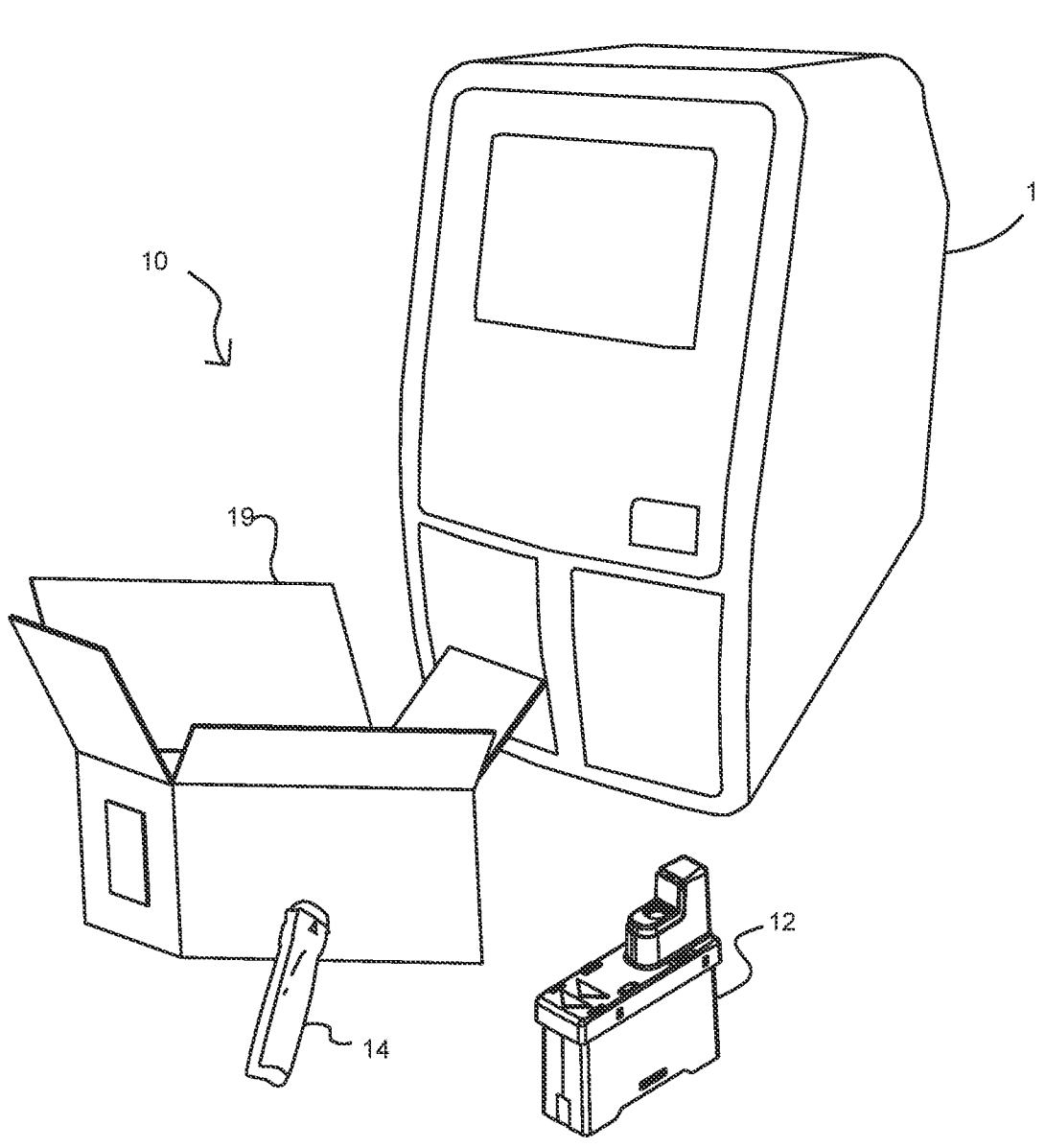
FIG. 1 is an illustration of a bioassay cartridge kit of the present invention for use with a scanner as shown.

Shown in FIG. 1 is an illustration of a fully inclusive and comprehensive cartridge kit 10 of the present invention shown next to a potential analyzer system 1. This cartridge kit 10 includes a modified ELISA cartridge 12 and fingerstick device 14 prepackaged for singular use with the separate analyzer system 1. Depending upon the specific test that the kit is designed for, according to various embodiments of the present invention, the cartridge kit may also include at least one pipette tip 20, sampler 18, and an integrated cuvette 16g which are discussed in greater detail below with respect to FIGS. 2-4. By providing these components as a unified kit in a single package 19, the present invention both reduces overall procedure time and reduces user error.

An exemplary analyzer system 1 capable of performing the assay as described herein is the ALLEGRO™ analyzer by NOVA Biomedical Corporation. An exemplary sampler and cartridge base capable of being used with a cartridge 12 as described herein is more fully described in U.S. Pat. No. 10,117,615 of NOVA Biomedical Corporation which is hereby incorporated in its entirety herein.

Modified ELISA Cartridge

Figure 3:
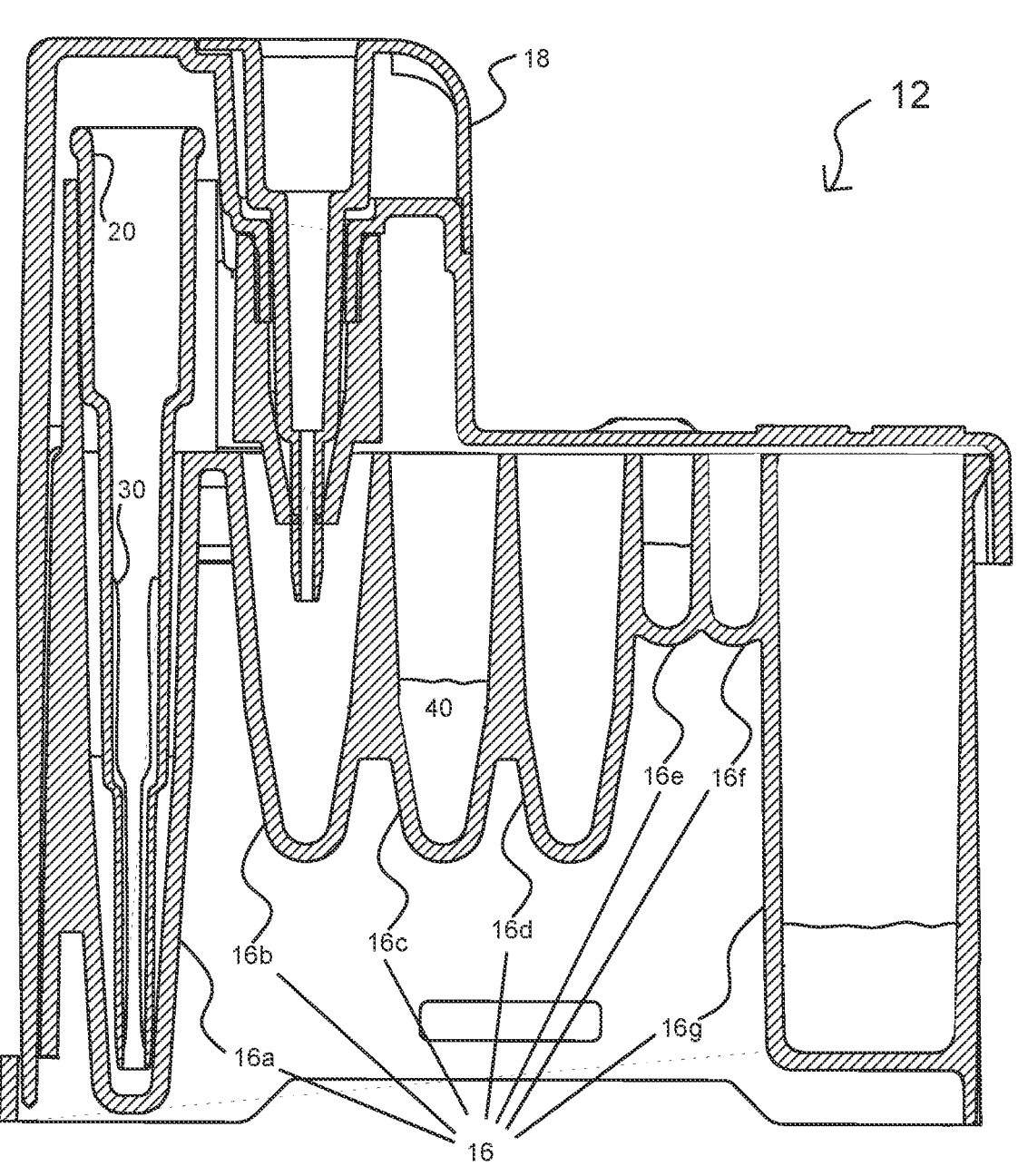
FIG. 3 is a cross-sectional view of a cartridge and pipette tip according to a further embodiment of the present invention.
Figure 4:
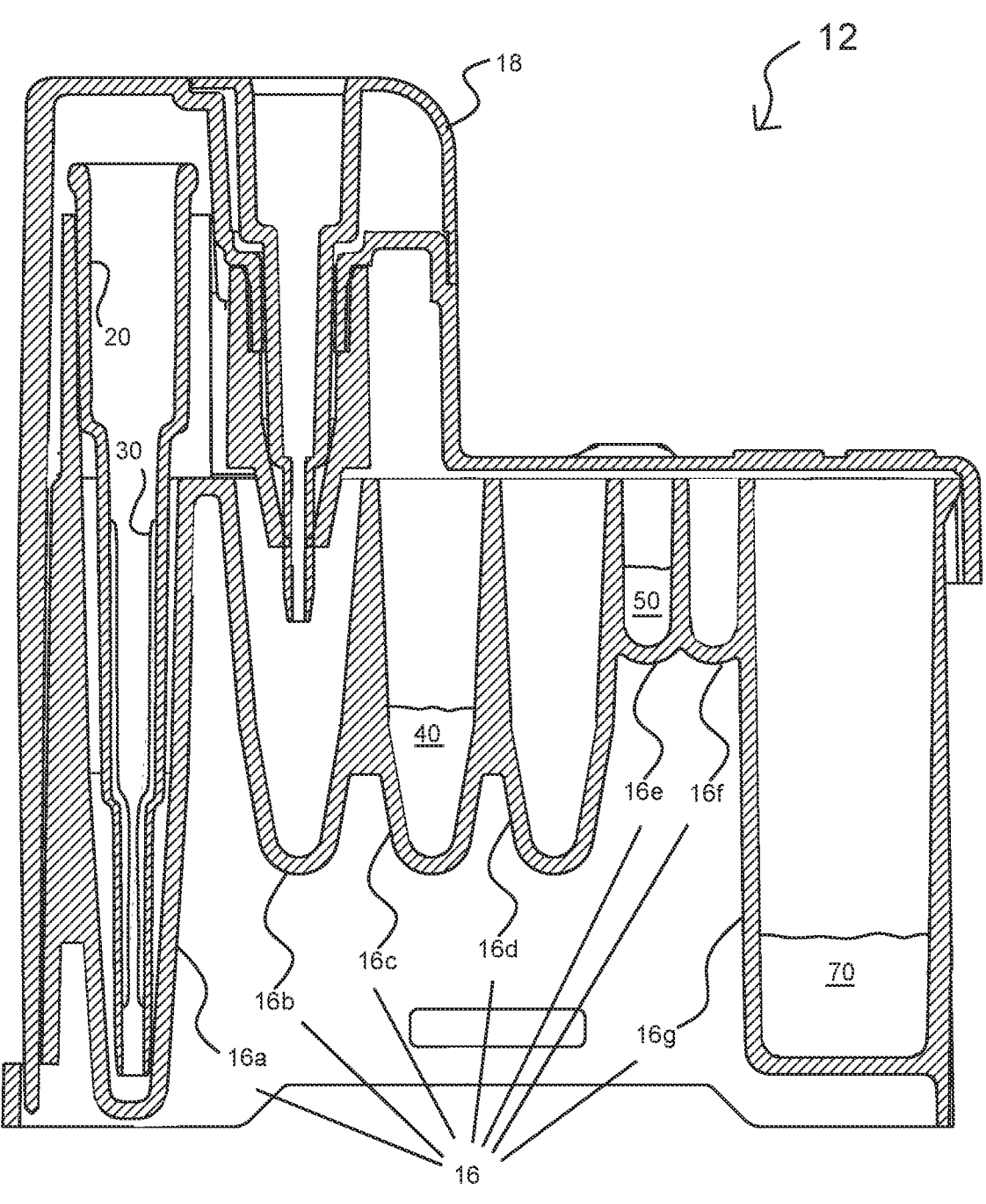
FIG. 4 is a cross-sectional view of a cartridge and pipette tip according to a further embodiment of the present invention.
Figure 5:
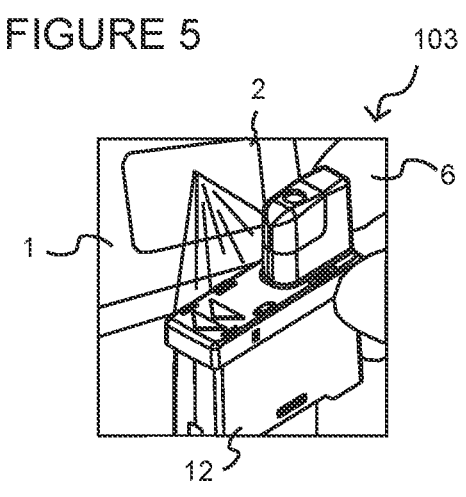
FIG. 5 is an illustration of a user scanning an identifier of a cartridge of the present invention.
Figure 6:
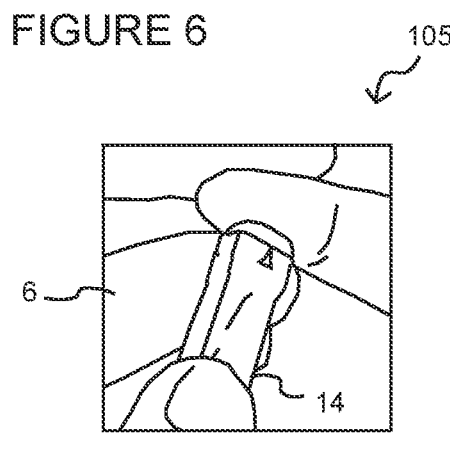
FIG. 6 is an illustration of a user using a fingerstick device to obtain a blood sample according to a method of the present invention.
Figure 7:
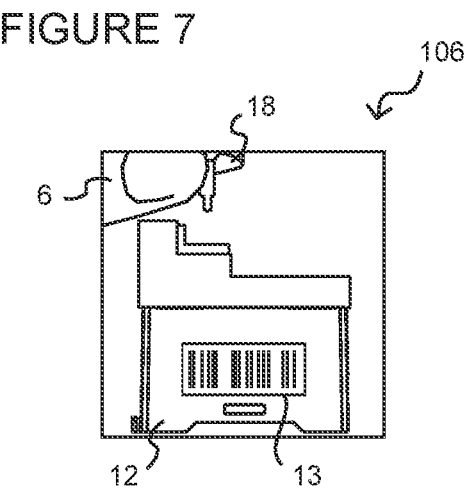
FIG. 7 is an illustration of a user retrieving a sampler from a cartridge of the present invention.
Figure 8:
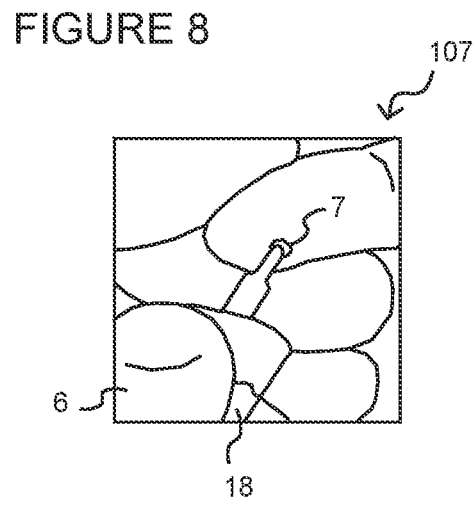
FIG. 8 is an illustration of a user filling a sampler from a cartridge of the present invention with a blood sample.
Figure 9:
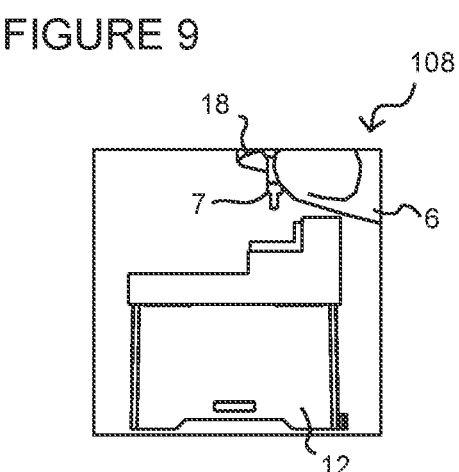
FIG. 9 is an illustration of a user replacing a filled sampler back to a cartridge of the present invention with a blood sample.
Figure 10:
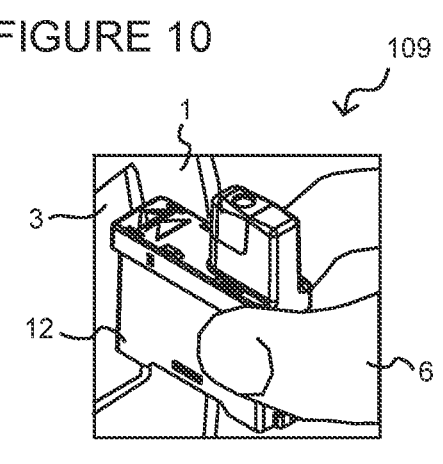
FIG. 10 is an illustration of a user placing the cartridge of the present invention with the filled sampler into the analyzer.
Figure 11:
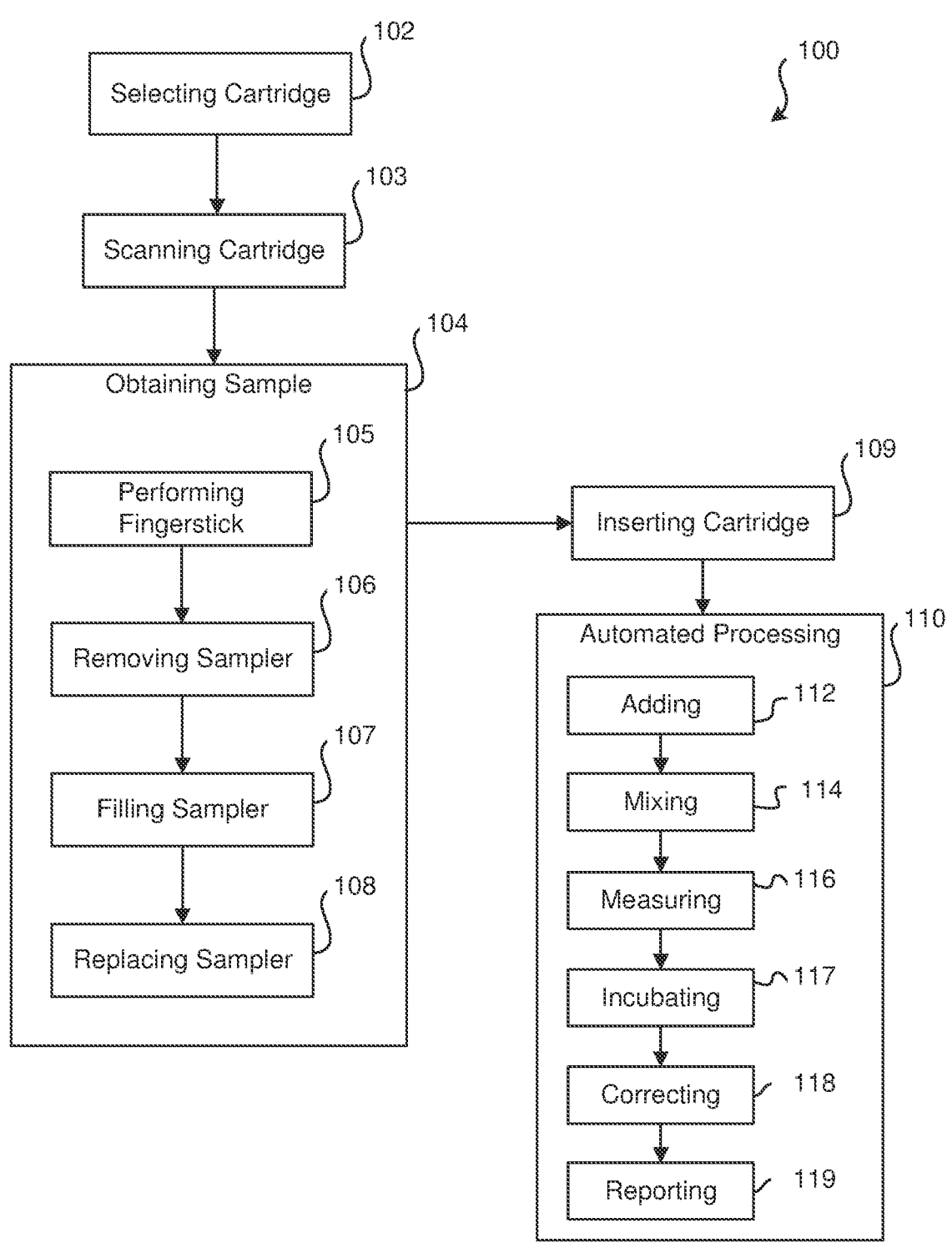
FIG. 11 illustrates an overview of the methods of the present invention.

An exemplary cartridge kit which may be used with the present inventive system and methodology may include a self-contained single-use disposable integrated cartridge 12 such as now will be described with further reference to FIGS. 2-4.

Figure 2:
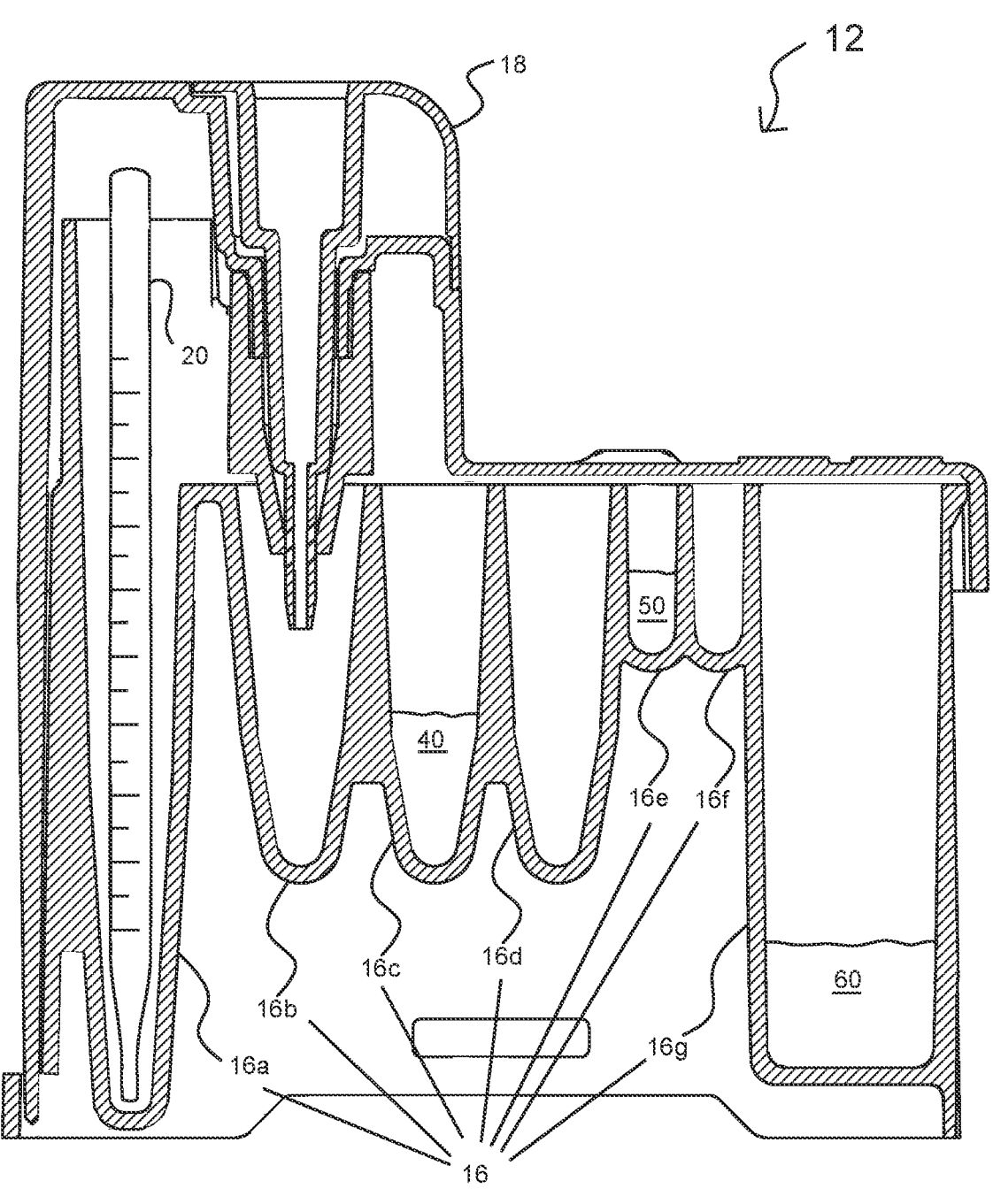
FIG. 2 is a cross-sectional view of a cartridge according to one embodiment of the present invention.

A first cartridge embodiment is illustrated in FIG. 2, and although not visible in the cross-sectional view, it has an identifier 13, such as a barcode, capable of identifying the specific type of cartridge (and thus ELISA) to the analyzer 1. This identifier 13 may be visible along a visible outer surface of the cartridge 12 and may also be provided along an outer surface of the main packaging 19. As discussed above, this packaging 19 may contain a cartridge 12 and at least one fingerstick lancet 14 or other similar devices capable of breaking the skin to obtain blood samples for testing.

In most embodiments, the cartridges 12 have a capillary sampler 18 which is a removable component of the cartridge 12 itself. Again, most cartridges 12 also have an integrated cuvette 16g, with sidewalls capable of facilitating optical measurement. However, it is also anticipated that the packaging 19 may contain a cartridge 12 which requires a separate disparate cuvette 16g provided in addition to the cartridge base. Regardless, these cartridges at the least, must have a series of wells 16 which are pre-loaded with components of the assay according to the present inventive method.

As may be seen in FIG. 2, the sampler 18 has a capillary element (not numbered) which is inserted through a corresponding capillary-receiving aperture in an extension portion top surface of a stepped extension portion of a cover extension of the disposable test cartridge 12 and is then seated in the stepped extension portion. During the insertion and setting process, the capillary tube of the sampler 18 is inserted through the lower portion aperture located in an apex end of the capillary wiper. Because the cross-sectional area of the lower portion aperture is smaller than the cross-sectional area of the capillary tube, the lower portion aperture acts like a squeegee against the outside surface of the capillary tube and prevents any sample inadvertently disposed on the outside surface of the capillary tube from entering and being deposited into the chamber 16b of the cartridge 12.

The capillary wiper of these cartridges 12 removes any sample 7 from the outside surface of the capillary tube. Erroneous results are thereby prevented from an "overfilling" of the appropriate well 16b in the test cartridge 12 with sample 7. Likewise, since the capillary tube is not wiped by the user, there is no, or very little, chance that any sample 7 within the capillary tube is removed inadvertently, which could lead to erroneous results from an "underfilling" of the well 16b in the test cartridge 12 with sample 7.

The pipette tip 20 provided in the first well 16a of a unitary cartridge 12 may be a pipette tip having measuring indicia along an outer surface as shown in FIG. 2. Alternatively, these tips may be beveled, extended, and/or graduated, as shown in FIGS. 3-4. Regardless, at least one pipette tip 20 in the first well 16 of the cartridge 12 will have a coating 30 along an interior wall. The various types of coatings 30 and the methods of providing these coatings are discussed in greater detail with reference to FIGS. 12-14 further below.

Method from User's Perspective

A general overview of a user's perspective is now discussed with reference to FIGS. 5-11. As shown here, initially, a modified ELISA cartridge or cartridge kit is selected by the user 102. After manually selecting a modified ELISA cartridge 102, the cartridge may be scanned by the analyzer to identify the selected assay 103. Then, obtaining the blood sample 104 may involve a simple fingerstick 105 to provide the required blood sample size. The ease by which a blood sample may be obtained in this step exhibits one of the benefits of the present inventive system over other prior art systems and methods which require venipuncture or other large blood sample size collection.

If the bioassay is identified initially, the capillary sampler may be removed from the cartridge 106, filled with the blood sample 107, and replaced in the specified cartridge 108, all within 30 seconds of performing the fingerstick 105. After replacing the filled sampler 108 back in the cartridge, the identifier may be scanned 103 by the analyzer, and the cartridge inserted into the analyzer 109. After loading the cartridge into the analyzer, the automated process 110 begins. Depending upon the selected bioassay, the automated process will then, according to the specified order of the bioassay components, involve automated steps of adding 112, mixing 114, measuring 116, incubating 117, correcting 118, and reporting 119 the results to the user or other designated individual.

Method of Coating Pipette Tips with CRP Antibodies

Various methods for preparing the pipette tips 20 according to the present inventive methods will now be discussed with particular reference to FIGS. 12-14. In general, preparing the pipette tips 20 as involves four main steps: coating with antibody solution 160, coating with blocking solution 170, coating with activity preservative solution 175, and drying the tips 180 so as to be ready for use. It should be understood that, notwithstanding the volume ranges disclosed, the volumes used will be dependent on the size of the capillary tips and the dimensions of the wells in the cartridge 12.

Figure 12:
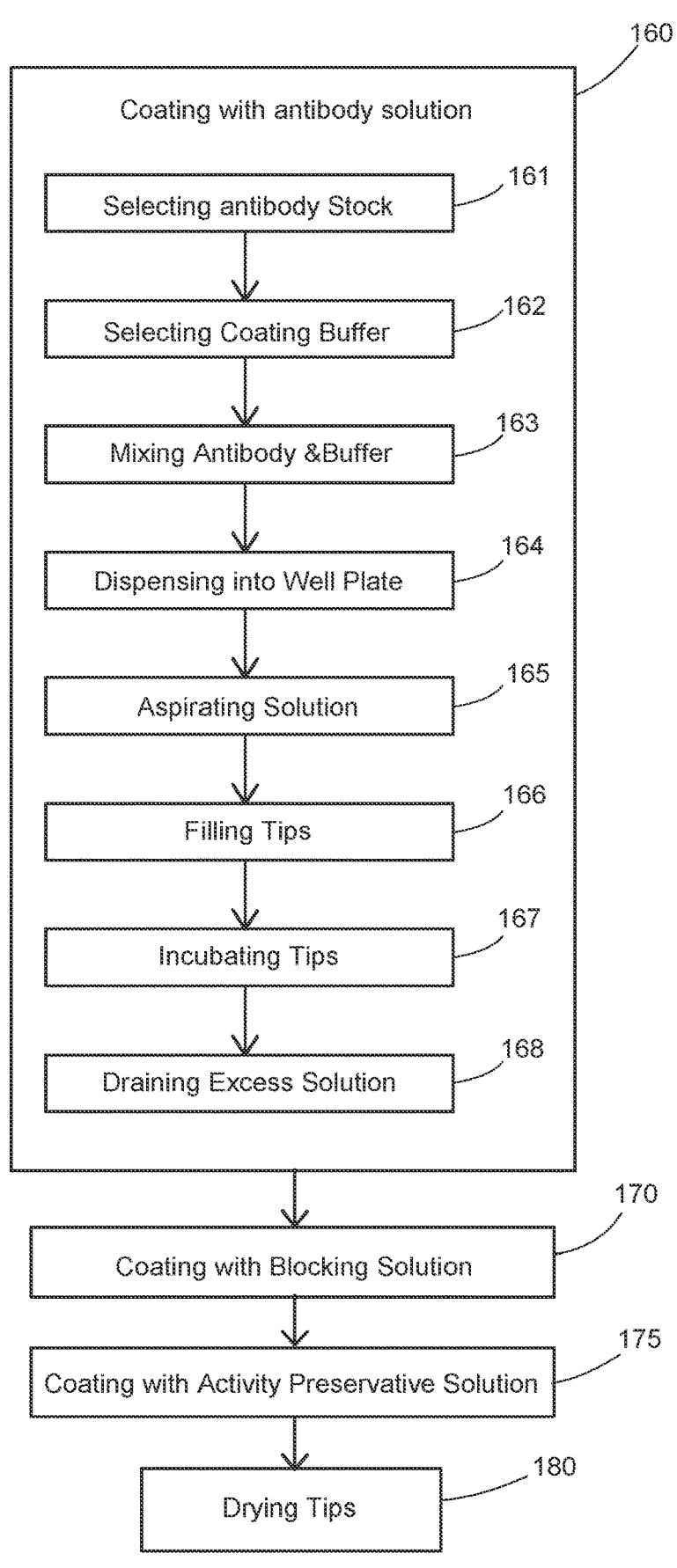
FIG. 12 illustrates an overview of the process of making the tip of the present invention.

FIG. 12 takes a closer look at the steps of the first main step, coating with antibody solution 160. According to one embodiment, this first main step began by selecting an antibody stock 161, in this case anti-CRP, and selecting a coating buffer 162, in this case 200 mM carbonate with pH 9.6. It is also to be understood that this would work with any similar protein such as antibody, antibody fragment, a recombinant protein, protein A, protein G, protein A/G, streptavidin, or recombinant proteins or fragments thereof, nucleic acid, polysaccharide, glycoprotein, peptidoglycans, molecular imprinted polymer or aptamer molecule. An antibody is the preferred affinity agent, as is commonly used in ELISA systems. Immobilization can be achieved by non-specific adsorption, or by covalent conjugation, as discussed above.

Similarly, while the coating buffers used in this method include carbonate/bicarbonate buffer system and sucrose, it is to be understood that similar coating buffers may also be used, such as phosphate buffered saline and buffers such as Tris buffered saline would also be acceptable.

Next, an antibody solution (anti-CRP, 5 ug/ml) was prepared by mixing the selected antibody stock and coating buffer 163. This solution was then dispensed into a 96 well plate 164. A multichannel pipette with attached pipette tips was used to aspirate the antibody solution into selected pipette tips until filled 166. Specifically, the amount of antibody solution is approximately between 100 portions-300 portions, preferably between 150 ul and 200 ul, and more preferably about 165 portions of between 50 ul-300 ul, preferably between 75 ul and 200 ul, and more preferably about 100 ul of antibody solution into selected pipette tips until filled 166. These filled pipette tips were then incubated 167 at between 10°-50° Celsius, preferably between 20°-30° Celsius, and more preferably room temperature, approximately, 22°-25° Celsius for a first time of between 200-2 minutes, preferably between 50-10 minutes, and more preferably, about 30 min. A layer of antibody solution was now adhered to an internal wall of the pipette tips. The excess solution was then dispensed out of the pipette tips and discarded. After draining the excess solution, the pipette tips further undergo coating with a blocking solution 170, then coating with an activity preservative solution 175, followed by drying the tips 180. The steps of coating with the blocking solution 170 and coating with the activity preservative solution is further illustrated in FIG. 13.

Figure 13:
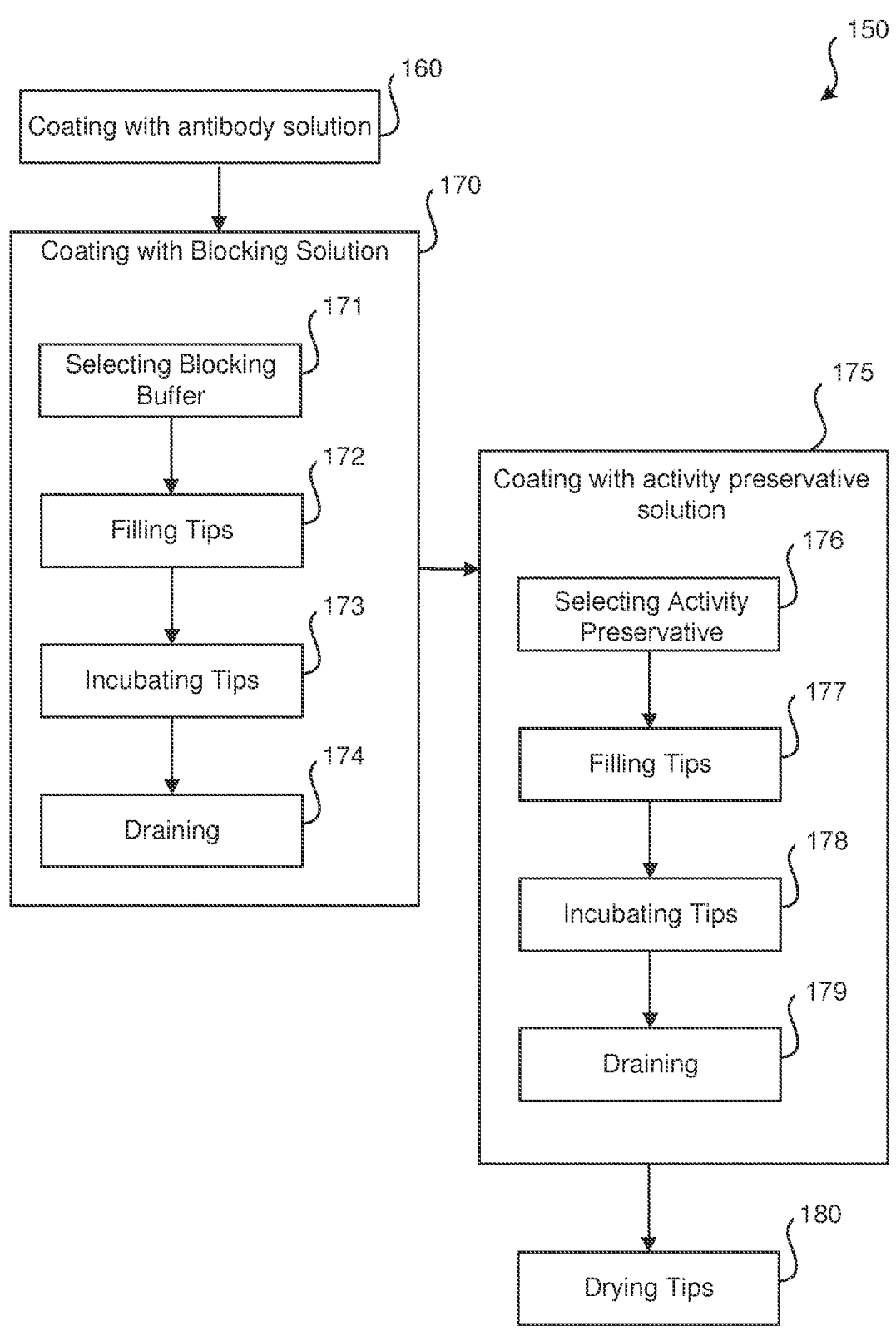
FIG. 13 illustrates a further continuation of the process in FIG. 12.

Turning now to FIG. 13, FIG. 13 takes a closer look at the next steps, which can be seen that the tips were next coated with blocking solution 170. Specifically, a blocking buffer is first selected 171. Blocking buffers which would be sufficient for this step would include phosphate buffered saline (PBS) containing between 0.5%-5% and, more preferably, 1% bovine serum albumin, gelatin, dried milk powder.

Next, the selected blocking buffer is aspirated into the tips, so that they are filled 172 with the selected blocking buffer, approximately between 50 ul and 1,000 ul, preferably between 100 ul and 400 ul, and more preferably about 200 ul of the selected blocking buffer. The filled tips are then incubated 173 for a second period of time, approximately between 2-30 minutes, preferably between 5-20 minutes, and more preferably, about 10 minutes. This incubation 173 is generally performed at temperatures between 10°-50° Celsius, preferably between 20°-30° Celsius, and more preferably, at room temperature of about 22°-25° Celsius. A layer of blocking buffer now being in position over the first layer of antibody solution, the excess blocking buffer is now drained and dispensed from the pipette tips 174.

Next, a coating of an activity preservative is provided 175. Specifically, an activity preservative is first selected 176. Activity preservatives which would be sufficient for this step would include between 0.5%-5% and, more preferably, 2% sucrose, trehalose, gelatin and other similar activity preservatives.

Next, the selected activity preservative is dispensed 177 into the tips already having first and second layers (i.e. coating of antibody solution and coating of blocking solution, respectively). However, this layer will completely cover the previous layers including along the top and bottom, so that they are still filled with between 50 ul and 1,000 ul, preferably between 100 ul and 400 ul, and more preferably about 110 ul of the selected activity preservative 176. The filled tips 177 are then incubated 178 for a third period of time, approximately 1 minute, at a temperature of between 10°-50° Celsius, preferably between 20°-30° Celsius, and more preferably, at approximately room temperature of about 22°-25° Celsius. A third layer of activity preservative is now in position over, and completely covering, the first and second layers of blocking buffer and antibody solution. After incubating, the excess amount of the activity preservative is now drained and dispensed from the pipette tips 179. The tips were then dried for between two to twenty hours, preferably between four and ten hours, and more preferably, about eight hours in a vacuum chamber 180.

Figure 14:
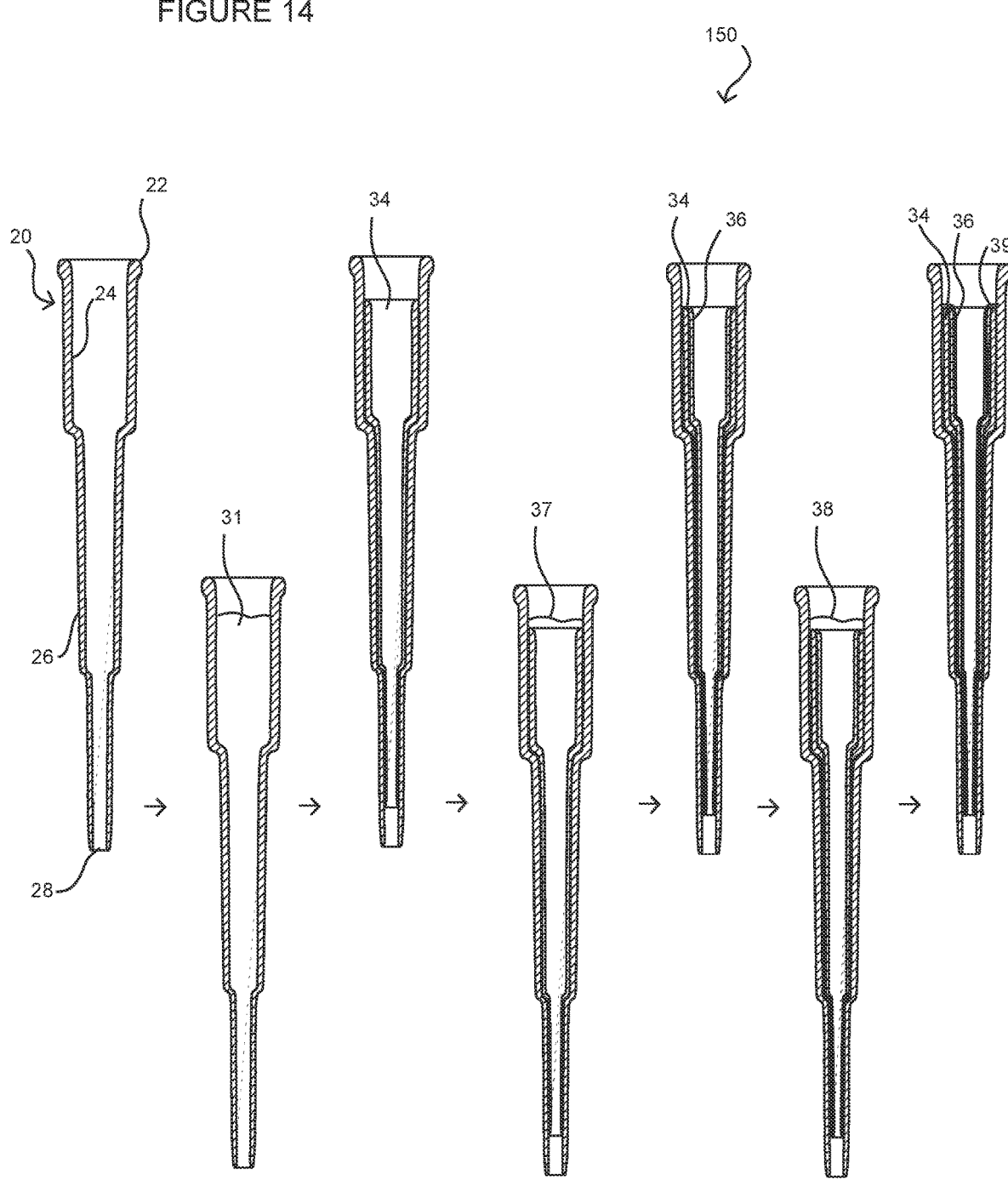
FIG. 14 illustrates aspects of the process in FIG. 12.

This process is visually shown in general in FIG. 14. Specifically, a cross-sectional view of a pipette tip 20 is shown during the process of preparing the tip 20 according to the above methods. At first, the pipette tip 20 is shown having an empty internal cavity 24 which extends from an opening 22 at a first end of the pipette tip 20 through a main portion 26 to a second opening 28 at a second ending of the pipette tip 20. The pipette tip 20 is then filled with the antibody solution 31 so that the internal cavity 24 is substantially filled.

When the excess material is drained away, a first layer 34 of the antibody solution 31 remains dried along the surface of the interior portion of the internal cavity 24. The empty volume of the internal cavity is reduced by the volume of the first layer 34 of the antibody solution 31 remaining. However, the coating buffer 37 is usually added to a vertical level higher than that of the antibody solution 31. Thus, when the coating buffer 37 is then added to the pipette tip 20, filling the pipette tip 20 still requires a similar amount of additional volume of coating buffer solution 37. After the excess buffer material is drained away, a layer of coating buffer 36 remains affixed along an interior facing surface of the first layer of the antibody solution 34 in the internal cavity 24. The activity preservation solution 38 is usually added to a vertical level higher than that of the coating buffer 36. Thus, when the activity preservation solution 38 is then added to the pipette tip 20, filling the pipette tip 20 still requires a similar amount of additional volume of activity preservation solution 38. After the excess activity preservation solution 38 is drained away, a layer of activity preservation material 39 remains affixed along an interior facing surface of the second layer of the coating buffer 36 in the internal cavity 24. Further layers of coating buffer 36, and/or the activity preservative 39 may be similarly applied according to the described methods above. It should be understood that the illustrated layers are thicker than they would be and is only shown for purposes of explanation and not to represent the actual relative thickness of each layer to the wall thickness of the pipette tip or to each other.

It is noted that specific amounts of the reagents are cited for preparation of the above pipette tips. It should be noted that any corresponding amounts are sufficient so long as a ratio of the surface area to volume is greater than 1/6 (units aside). Where a surface area of a tip=$\pi rh + \pi r^2$ and the volume of a tip=$\frac{1}{3}\pi r^2 l$, where r=large radius of the tip, l=length of the tip, and h=hypotenuse of the tip. For example, for a tip with a radius of 3 mm, and length of 10.6 mm, the surface area along the internal sides of the pipette tip becomes at least 132.1 mm² for a volume of 100 mm³ for a surface area to volume ratio of 132:100 or 1.32 to 1.

Alternatively, for a tip with a base radius of 7.87 mm, and length of 58.42 mm, the surface area along the internal sides of the pipette tip becomes 1652 mm² and the tip can hold a volume of 3789 mm³ for a surface area to volume ratio of 1652:3789 or 0.43:1. The greater the exposed surface area of the tips with reagents, the greater the increased rate of reaction overall, which can reduce the required response times. However, the surface area to volume ratio need not be greater than one. Studies have shown that it is sufficient for the surface to volume ratio to be between 5 to 1/5, more preferably between 1 to 1/4, and more preferably about 0.43.

General Assay Reagents and Additional Components

A first reagent mixture according to one embodiment has a pH stabilizer, ionic catalyst control agent, ionic intracellular inhibitory control agent, detergent, negative control agent, chelating agent, and biocide preservative.

A second reagent mixture according to one embodiment has a pH stabilizer, ionic catalyst control agent, ionic intracellular inhibitory control agent, chelating agent, and biocide preservative.

A third reagent mixture according to one embodiment has an antibody, conjugate stabilizing agent, and negative control.

A fourth reagent mixture according to one embodiment has at least one of a chromogenic substrate or visualizing reagent.

A first reagent mixture according to one embodiment has a pH stabilizer, ionic catalyst control agent, ionic intracellular inhibitory control agent, detergent, negative control agent, chelating agent, and biocide preservative.

A second reagent mixture according to one embodiment has a pH stabilizer, ionic catalyst control agent, ionic intracellular inhibitory control agent, chelating agent, and biocide preservative.

A third reagent mixture according to one embodiment has an antibody, conjugate stabilizing agent, and negative control.

A fourth reagent mixture according to one embodiment has at least one of a chromogenic substrate or visualizing reagent.

An exemplary pH stabilizer which may be used in the present inventive method is a 10 mM phosphate buffer, which facilitates in maintaining a pH of 7.4.

An exemplary ionic catalyst control agent which may be used in the present inventive method is a 138 mM NaCl solution.

An exemplary ionic intracellular inhibitory control agent which may be used in the present inventive method is a 2.7 mM KCl solution.

An exemplary biocide preservative which may be used in the present inventive method is 0.03% biocide preservative sold under the trademark ProClin™ 300 which is water soluble, comprised of 3% CMIT/MIT in a salt-free proprietary glycol containing an alky carboxylate stabilizer.

An exemplary chelating agent which may be used in the present inventive method is 5 mM ethylenediaminetetraacetic acid (EDTA).

An exemplary detergent which may be used in the present inventive method is 0.1% detergent sold under the trademark Triton™ X-100(TX100), which is one of the most widely used nonionic surfactants for lysing cells to extract protein and other cellular organelles or to permeabilize the living cell membrane for transfection.

An exemplary emulsifying agent which may be used in the present inventive method is 0.05% of an emulsifying agent sold under the trademark Tween® 20™ (polyoxyethylene sorbitan monolaurate).

An exemplary negative control which may be used in the present inventive method is Mouse IgG available from Meridian Life Science, Inc. of Tennessee, which typically constitutes 75% of serum immunoglobulins and are synthesized and secreted by plasma B cells.

An antibody which may be used in the present inventive method is anti CRP-antibody-HRP (250 ng/mL), a C-Reactive Protein (CRP) primary antibody conjugated with horseradish peroxidase (HRP).

CRP is a member of the pentraxin family of proteins that are characterized by a cyclic pentameric structure. Human CRP gene encodes a 224 amino acids precursor. The mature human CRP protein has 206 amino acids that are non-covalently linked to form the pentamer. Human CRP shares 71% and 64% amino acid sequence homology with mouse and rat respectively.

CRP, synthesized by hepatocytes, is a major acute phase serum protein in human. IL-6, IL-1 and glucocorticoids are the major inducer of the CRP gene. In response to infection, inflammation or tissue damage, the level of CRP in human serum can increase 1,000-fold within 24-48 hours. It will come back to base level of less than 1 μg/mL very fast. Human CRP is an acute-phase serum protein that plays a role in the first line in host innate host defense. Like other pentraxins, CRP exhibits $Ca^{++}$—dependent binding to ligands. Phosphocholine (PCh), a constituent of many bacterial and fungal walls, is a principal ligand of CRP.

CRP also binds to the membrane of injured cells, membrane and nuclear components of necrotic and apoptotic cells. Upon binding with the ligands, CRP is recognized by C1q and initiates the activation of complement cascade. Ligand bound CRP also binds to Fc gamma RI and Fc gamma RIIa on phagocytes and activates phagocytotic responses. In addition to phagocytosis, CRP also can induce production of hydrogen peroxide and inflammatory cytokines, such as IL-1, IL-6 and TNF-alpha by monocytes. With these functions, human CRP is an important serum protein for anti-bacterial pathogen and clearance of damaged and apoptotic cells. However, in mouse, CRP is expressed at very low level and is not an acute phase reactant. Serum amyloid P component (SAP), another pentraxin, is the major acute phase serum protein in mice. It has been shown that high levels of CRP in humans is associated with an increased risk of cardiovascular diseases.

A conjugate stabilizing agent which may be used in the present inventive method is a conjugate stabilizing agent sold under the trademark StabilZyme™, which is a multipurpose HRP conjugate stabilizing solution designed to maintain the conformation of antibody/antigen conjugates, antibody coated particles and unmodified proteins that are commonly used in immunoassays.

A chromogenic substrate or visualizing reagent which may be used in the present inventive method is 3,3',5,5'-tetramethylbenzidine (TMB).

An antifoaming/defoaming agent may be used in the presentive inventive method. An example of such an agent is sold under the trademark Foam Away™ and available from ThermoFisher Scientific.

Example—CRP Results Illustrated in FIG. 15

Assay cartridge and cuvette preparation included preparation of pipette tips according to the above methods with capture anti-CRP antibodies. Specifically, during the preparation 150 of pipette tips 20, capture anti-CRP antibodies were bound to the inside of pipette tips 20 otherwise capable of holding 300 ul volume of solution.

Cartridges were prepared according to the above methods by dispensing the following amounts into the indicated wells:

| Well | Reagent Mixtures/Components |
|---|---|
| 1 (16a) | Pipette tip with capture anti-CRP antibodies |
| 2 (16b) | [initially empty] 5 uL of sample |
| 3 (16c) | First Reagent Mixture: 380 uL of 10 mM phosphate buffer, 138 mM NaCl, 2.7 mM KCl; pH 7.4, 0.05% polysorbate-type nonionic surfactant, 0.03% biocide preservative, 5 mM EDTA, 0.1% nonionic surfactant, 0.1 mg/ml Mouse IgG |
| 4 (16d) | Second Reagent Mixture: 380 uL of 10 mM phosphate buffer, 138 mM NaCl, 2.7 mM KCl; pH 7.4, 0.05% polysorbate-type nonionic surfactant, 0.03% biocide preservative, 5 mM EDTA |
| 5 (16e) | Third Reagent Mixture: 130 ul of anti CRP-antibody-HRP (250 ng/mL), HRP conjugate stabilizing agent, 0.1 mg/ml Mouse IgG |
| 6 (16f) | Fourth Reagent Mixture: 130 uL of 10 mM phosphate buffer, 138 mM NaCl, 2.7 mM KCl; pH 7.4, 0.05% polysorbate-type nonionic surfactant, 0.03% biocide preservative, 5 mM EDTA |
| Cuvette (16g) | Fifth Reagent Mixture: 300 uL 3,3',5,5'-tetramethylbenzidine |

After preparation of the cartridges, the blood samples were obtained 104 according to the above described methods via the capillary sampler 18. After the analyzer identifies the selected bioassay, the cartridge is loaded into the analyzer, and the automated process 110 begins. Specifically, the analyzer employs a pipette arm and express gravity to transfer the reagents or blood sample 112 according to the specified automated process 110.

In this bioassay, the automatic steps include adding 112, mixing 114, measuring 116, incubating 117, correcting 118, and reporting 119 the results to the user or other designated individual. The assay was initiated by transferring 290 ul of the first reagent amount from the third well 16c into the second well 16b.

Next, 5 ul of blood sample was then expressed 112 from the capillary sampler 18 into the second well 16b. The pipette tip with the antibodies from the first well 16a was then used to aspirate 100 uL of sample from the second well. This sample was then held 117 inside the pipette tip for 60 seconds after which the lysed blood sample was then discarded back into the second well 16b.

A first wash was then performed in which 130 uL of the fourth reagent from the sixth well 16f was then aspirated and then discarded back again. A second wash was then performed with 55 uL of the second reagent from the fourth well 16d followed by a 75 uL air gap. This was then discarded into the third well 16c. This was repeated as a third wash.

Next, analyte labeling with anti CRP-HRP was performed by mixing 114 and aspirating 100 uL of the third reagent from the fifth well 16e and holding 117 for 4 minutes. This was then discarded back into the fifth well 16e.

Four additional washes of the pipette tip were then performed. In the fourth wash, 130 uL of the first reagent were aspirated 114 and then discarded back into the third well 16c. In the fifth wash, 65 uL of the second reagent were aspirated 114 from the fourth well 16d, followed by a 65 uL air gap. This was also then discarded into the third well 16c. In the sixth wash, 65 uL of the second reagent was aspirated 114 from the fourth well 16d, followed by a 65 uL air gap. This was also then discarded into the third well 16c. In the seventh wash, 130 uL of the third reagent was aspirated 114 from the fourth well 16d. This was then discarded into the fourth well 16d. Next, 100 ul of the fifth reagent was then aspirated 114 from the cuvette 16g, held 117 for 2 minutes, and then discarded back to the cuvette 16g and mixed 114. The sample was then read 116 at 660 nm as described herein elsewhere.

This procedure was repeated for six different concentrations of CRP. Data is shown in the table below:

| CRP (mg/L) | OD660 nm |
|---|---|
| 0 | 0.0045 |
| 4.25 | 0.0897 |
| 17.97 | 0.2658 |
| 56.92 | 0.6953 |
| 95.87 | 0.8837 |
| 203.28 | 1.0881 |

As previously mentioned, this data is also visually illustrated in FIG. 15.

Example—Cystatin Results Illustrated in FIG. 16

Assay cartridge and cuvette preparation included preparation of pipette tips according to the above methods with capture anti-cystatin C antibodies. Specifically, during the preparation 150 of pipette tips 20, capture anti-Cystatin C antibodies were bound to the inside of pipette tips 20 otherwise capable of holding 300 ul volume of solution.

Cartridges were prepared according to the above methods by dispensing the following amounts into the indicated wells:

| Well | Reagent Mixtures/Components |
|---|---|
| 1 (16a) | Pipette tip with capture anti-Cystatin C antibodies |
| 2 (16b) | [initially empty] 5 uL of sample |
| 3 (16c) | First Reagent Mixture: 380 uL lysing solution (0.002% saponin, 0.01% low foaming agent, 0.02% sodium azide (NaN₃) |
| 4 (16d) | Second Reagent Mixture: 380 uL 10 mM PBS, 0.05% polysorbate-type nonionic surfactant, 0.03% biocide preservative |
| 5 (16e) | Third Reagent Mixture: 110 ul anti cystatin C-antibody-HRP(1:1000 of 1 ug/mL), HRP conjugate stabilizing agent, 0.5% antifoaming/defoaming agent |
| 6 (16f) | [Empty] |
| Cuvette (16g) | Fourth Reagent Mixture: 300 uL 3,3',5,5'-tetramethylbenzidine |

After preparation of the cartridges, samples with different concentrations of cystatin were obtained 104 via the capillary sampler 18. After the analyzer identifies the selected bioassay, the cartridge is loaded into the analyzer, and the automated process 110 begins. Specifically, the analyzer employs a pipette arm and express gravity to transfer the reagents or blood sample 112 according to the specified automated process 110.

In this bioassay, the automated steps include adding 112, mixing 114, measuring 116, incubating 117, correcting 118, and reporting 119 the results to the user or other designated individual. The assay was initiated by transferring 290 ul of the first reagent amount from the third well 16c into the second well 16b.

Next, 5 ul of sample was then expressed 112 from the capillary sampler 18 into the second well 16b. The pipette tip with the antibodies from the first well 16a was then used to aspirate 75 uL of diluted blood sample from the second well 16b to the sixth well 16f. Next, 75 uL of the third reagent from the fifth well 16e was then also moved 112 from the fifth well 16e to the sixth well 16f.

Then, analyte labeling was performed by mixing 114 the reagent mixtures and diluted sample in the sixth well 16f by being pipetted up and down three times. Then, 100 uL of this sample mixture was then aspirated into a pipette tip and incubated 117 for 60 seconds after which the lysed blood sample mixture was then discarded back into the sixth well 16f.

Four washes of the pipette tip were then performed. In the first wash, 50 uL of the first reagent were aspirated 114 and then discarded back into the third well 16c. In the second wash, 110 uL of the second reagent were aspirated 114 from the fourth well 16d, followed by a 20 uL air gap. This was also then discarded into the third well 16c. In the third wash, 110 uL of the second reagent was aspirated 114 from the fourth well 16d, followed by a 20 uL air gap. This was also then discarded into the third well 16c. In the fourth wash, 110 uL of the third reagent was aspirated 114 from the fourth well 16d. This was then discarded into the second well 16b.

Next, 100 ul of the fourth reagent was then aspirated 114 from the cuvette 16g, held 117 for 2 minutes, and then discarded back to the cuvette 16g and mixed 114. The sample was then read 116 at 660 nm as described herein elsewhere.

This procedure was repeated for seven different concentrations of known cystatin concentrations. Data is shown in the table below:

| Cystatin (mg/L) | OD660 nm |
|---|---|
| 0 | 0.0173 |
| 0.25 | 0.1043 |
| 0.50 | 0.2541 |
| 1.00 | 0.4780 |
| 2.00 | 0.8195 |
| 4.00 | 1.3768 |
| 8.00 | 1.9523 |

As previously mentioned, this data is also visually illustrated in FIG. 16.

Example—ALT Results Illustrated in FIG. 17

Assay cartridge and cuvette preparation included preparation of pipette tips according to the above methods except-ing that this time the coating was done with anti-alanine aminotransferase (anti-ALT) antibodies. Specifically, during the preparation 150 of pipette tips 20, capture anti-ALT antibodies were bound to the inside of pipette tips 20 otherwise capable of holding 300 ul volume of solution.

Cartridges were prepared according to the above methods by dispensing the following amounts into the indicated wells:

| Well | Reagent Mixtures/Components |
|---|---|
| 1 (16a) | Pipette tips with capture anti-ALT antibodies |
| 2 (16b) | [initially empty] 5 uL of sample |
| 3 (16c) | First Reagent Mixture: 380 uL 10 mM PBS, 0.05% polysorbate-type nonionic surfactant |
| 4 (16d) | Second Reagent Mixture: 380 uL 10 mM PBS, 0.05% polysorbate-type nonionic surfactant |
| 5 (16e) | Third Reagent Mixture: 130 uL anti ALT antibody-HRP(2 ug/mL) in HRP conjugate stabilizing agent |
| 6 (16f) | Fourth Reagent Mixture: 130 uL 10 mM PBS, 0.05% polysorbate-type nonionic surfactant |
| Cuvette (16g) | Fifth Reagent Mixture: 300 uL 3,3',5,5'-tetramethylbenzidine |

15
16

After preparation of the cartridges, samples with different concentrations of ALT were obtained 104 via the capillary sampler 18. After the analyzer identifies the selected bioassay, the cartridge is loaded into the analyzer, and the automated process 110 begins. Specifically, the analyzer employs a pipette arm and express gravity to transfer the reagents or blood sample 112 according to the specified automated process 110.

In this exemplary bioassay, the automated steps include adding 112, mixing 114, measuring 116, incubating 117, correcting 118, and reporting 119 the results to the user or other designated individual thereafter. The assay was initiated by transferring 290 ul of the first reagent amount from the third well 16c into the second well 16b.

Next, 5 ul of sample was then expressed 112 from the capillary sampler 18 into the second well 16b. The pipette tip with the antibodies from the first well 16a was then used to aspirate 100 uL of lysed blood sample from the second well 16b. This sample was then held 117 inside the pipette tip for 10 minutes after which the lysed blood sample was then discarded back into the second well 16b.

A first wash was then performed in which 130 uL of the fourth reagent from the third well 16c was then aspirated and then discarded back again. A second wash was then performed with 55 uL of the second reagent from the fourth well 16d followed by a 75 uL air gap. This was then discarded into the third well 16c. This was repeated as a third wash.

Next, analyte labeling was performed by mixing 114 and aspirating 100 uL of the third reagent from the fifth well 16e and holding 117 for 4 minutes. This was then discarded back into the fifth well 16e.

Four additional washes of the pipette tip were then performed. In the fourth wash, 130 uL of the first reagent were aspirated 114 from the third well 16c and then discarded back into the third well 16c. In the fifth wash, 65 uL of the second reagent were aspirated 114 from the fourth well 16d, followed by a 65 uL air gap. This was also then discarded into the third well 16c. In the sixth wash, 65 uL of the second reagent was aspirated 114 from the fourth well 16d, followed by a 65 uL air gap. This was also then discarded into the third well 16c. In the seventh wash, 130 uL of the second reagent was again aspirated 114 from the fourth well 16d. This was then once again discarded into the fourth well 16d. Next, 100 ul of the fifth reagent was then aspirated 114 from the cuvette 16g, held 117 for 10 minutes, and then discarded back to the cuvette 16g and mixed 114. The sample was then read 116 at 660 nm as described herein elsewhere.

This procedure was repeated for three different concentrations of alanine aminotransferase concentrations. Data is shown in the table below:

| ALT Conc. (U/L) | OD660 |
|---|---|
| 0 | 0.0627 |
| 250 | 0.4169 |
| 1000 | 0.6375 |

Examples—AST Results For Pretreatment & Additional Secondary Optional Pretreatment—Illustrated in FIG. 18

In FIG. 18, results illustrating the additional benefits accorded by a secondary optional pretreatment compared to the present method are shown by comparing the analysis of additional plasma treated tips and the present method treated tips for aspartate amino transferase (AST) antibodies. Additional Pretreatment of pipette tips in plasma chamber prior to antibody coating according to the normal inventive method discussed herein may result in improved antibody binding to pre-treated pipette tips compared to pipette tips used as provided by manufacturer. This increased antibody binding is then reflected in increased assay signal. Assay cartridge and cuvette preparation included preparation of pipette tips according to a modified method as discussed above. This coating procedure was substantially similar to that described above, excepting that the additional procedure now includes an additional optional pretreatment (referred to as plasma treatment). The following description of both the coating treatment and additional plasma coating treatment was performed with capture anti-aspartate amino transferase (anti-AST) antibodies.

Specifically, during the preparation 150 of pipette tips 20, capture anti-AST antibodies were bound to the inside of pipette tips 20 otherwise capable of holding 300 ul volume of solution. Initially, 100 uL of antibody solution having 5 ug/mL capture AB in KPL buffer was aspirated and held for two hours. The portion that did not bind to the side walls was then discarded. Next, 200 uL of 10 mM PBS and 0.05% Tw-20 was aspirated into the pipette tips, a portion of this bound to the side walls of the pipette tips. The portion that did not bind to the side walls was then discarded. Finally, 200 uL of 10 mM PBS, 0.05% Tw-20, 0.1% BSA was aspirated into the pipette tips and incubated for 5 minutes forming a third layer along the sidewalls of the pipette tips. The portion that did not bind to the side walls was then discarded.

Cartridges were prepared according to the above methods by dispensing the following amounts into the indicated wells:

| Well | Reagents/Components |
|---|---|
| 1 (16a) | Pipette tip with capture anti-AST antibodies |
| 2 (16b) | [initially empty] 5 uL of sample |
| 3 (16c) | First Reagent Mixture: 380 uL 10 mM PBS, 0.05% polysorbate-type nonionic surfactant, 0.1% Bis(trimethylsilyl)acetamide (BSA) |
| 4 (16d) | Second Reagent Mixture: 380 uL 10 mM PBS, 0.05% polysorbate-type nonionic surfactant |
| 5 (16e) | Third Reagent Mixture: 130 uL anti AST-antibody-HRP (2 ug/mL) in HRP conjugate stabilizing agent |
| 6 (16f) | Fourth Reagent Mixture: 130 uL 10 mM PBS, 0.05% polysorbate-type nonionic surfactant |
| Cuvette (16g) | Fifth Reagent Mixture: 300 uL 3,3',5,5'-tetramethylbenzidine |

After preparation of the cartridges, the testing samples were obtained 104 and placed into the capillary sampler 18. After the analyzer identifies the selected bioassay, the cartridge is loaded into the analyzer, and the automated process 110 begins. Specifically, the analyzer employs a pipette arm and express gravity to transfer the reagents or blood sample 112 according to the specified automated process 110.

In this exemplary bioassay, the automated steps include adding 112, mixing 114, measuring 116, incubating 117, correcting 118, and reporting 119 the results to the user or other designated individual thereafter. The assay was initiated by transferring 290 ul of the first reagent amount from the third well 16c into the second well 16b.

Next, 8 ul of AST calibrator was then expressed 112 from the capillary sampler 18 into the second well 16a. The pipette tip with the antibodies from the first well 16a was then used to aspirate 100 uL of sample from the second well. This sample was then held 117 inside the pipette tip for 10 minutes after which the sample was then discarded back into the second well 16b.

A first wash was then performed in which 130 uL of the fourth reagent from the sixth well 16f was then aspirated and then discarded back again. A second wash was then performed with 55 uL of the second reagent from the fourth well 16d followed by a 75 uL air gap. This was then discarded into the third well 16c. This was repeated as a third wash.

Next, analyte labeling was performed by aspirating 100 uL of the third reagent from the fifth well 16e and holding 117 for 10 minutes. This was then discarded back into the fifth well 16e.

Four additional washes of the pipette tip were then performed. In the fourth wash, 130 uL of the first reagent were aspirated 114 from the third well 16c and then discarded back into the third well 16c. In the fifth wash, 65 uL of the second reagent were aspirated 114 from the fourth well 16d, followed by a 65 uL air gap. This was also then discarded into the third well 16c. In the sixth wash, 65 uL of the second reagent was aspirated 114 from the fourth well 16d, followed by a 65 uL air gap. This was also then discarded into the third well 16c. In the seventh wash, 130 uL of the second reagent was again aspirated 114 from the fourth well 16d. This was then once again discarded into the fourth well 16d. Next, 100 ul of the fifth reagent was then aspirated 114 from the cuvette 16g, held 117 for 10 minutes, and then discarded back to the cuvette 16g and mixed 114. The sample was then read 116 at 660 nm as described herein elsewhere.

This procedure was repeated for eight different concentrations of AST for each of the plasma-treated tips and treated tips. Data is shown in the table below:

| AST conc (U/L) | Plasma Treated tips | Treated tips |
| --- | --- | --- |
| 0 | 0.091 | 0.051 |
| 187.5 | 0.414 | 0.101 |
| 375 | 0.658 | 0.146 |
| 937.5 | 1.217 | 0.254 |
| 1875 | 1.637 | 0.36 |
| 3750 | 2.096 | 0.449 |
| 9375 | 2.669 | 0.64 |
| 18750 | 3.1 | 0.882 |

Example—hs-CRP Results Illustrated in FIG. 19

Assay cartridge and cuvette preparation included preparation of pipette tips according to the above methods with capture anti-CRP antibodies. Specifically, during the preparation 150 of pipette tips 20, capture anti-CRP antibodies were bound to the inside of pipette tips 20 otherwise capable of holding 300 ul volume of solution.

Cartridges were prepared according to the above methods by dispensing the following amounts into the indicated wells:

| Well | Reagents/Components |
| --- | --- |
| 1 (16a) | Pipette tip with capture anti-CRP antibodies |
| 2 (16b) | [Initially Empty] 5 uL of sample |

-continued

| Well | Reagents/Components |
| --- | --- |
| 3 (16c) | First Reagent Mixture: 380 uL 10 mM PBS, 0.05% polysorbate-type nonionic surfactant, 0.1% nonionic surfactant, 0.03% biocide preservative, 5 mM EDTA |
| 4 (16d) | Second Reagent Mixture: 380 uL 10 mM PBS, 0.05% polysorbate-type nonionic surfactant, 0.03% biocide preservative, 5 mM EDTA |
| 5 (16e) | Third Reagent Mixture: 130 uL Antibody-HRP (250 ng/mL) in HRP conjugate stabilizing agent, 100 ug/mL Mouse IgG |
| 6 (16f) | Fourth Reagent Mixture: 130 uL 10 mM PBS, 0.05% polysorbate-type nonionic surfactant, 0.03% biocide preservative, 5 mM EDTA |
| Cuvette(16g) | Fifth Reagent Mixture: 300 uL 3,3',5,5'-tetramethylbenzidine |

After preparation of the cartridges, the testing samples were obtained 104 and placed into the capillary sampler 18. After the analyzer identifies the selected bioassay, the cartridge is loaded into the analyzer, and the automated process 110 begins. Specifically, the analyzer employs a pipette arm and express gravity to transfer the reagents or blood sample 112 according to the specified automated process 110.

In this exemplary bioassay, the automated steps include adding 112, mixing 114, measuring 116, incubating 117, correcting 118, and reporting 119 the results to the user or other designated individual thereafter. The assay was initiated by transferring 290 ul of the first reagent amount from the third well 16c into the second well 16b.

Next, 5 ul of a sample with highly sensitive C-reactive protein (hs-CRP) was then expressed 112 from the capillary sampler 18 into the second well 16b. The pipette tip with the antibodies from the first well 16a was then used to aspirate 100 uL of sample from the second well 16b. This sample was then held 117 inside the pipette tip and then discarded back into the second well 16b.

A first wash was then performed in which 130 uL of the fourth reagent from the sixth well 16f was then aspirated and then discarded back again. A second wash was then performed with 55 uL of the second reagent from the fourth well 16d followed by a 75 uL air gap. This was then discarded into the third well 16c. This was repeated as a third wash.

Next, analyte labeling was performed by aspirating 100 uL of the third reagent from the fifth well 16e and holding 117 for 3 minutes. This was then discarded back into the fifth well 16e.

Four additional washes of the pipette tip were then performed. In the fourth wash, 130 uL of the first reagent were aspirated 114 from the third well 16c and then discarded back into the third well 16c. In the fifth wash, 65 uL of the second reagent were aspirated 114 from the fourth well 16d, followed by a 65 uL air gap. This was also then discarded into the third well 16c. In the sixth wash, 65 uL of the second reagent was aspirated 114 from the fourth well 16d, followed by a 65 uL air gap. This was also then discarded into the third well 16c. In the seventh wash, 130 uL of the second reagent was again aspirated 114 from the fourth well 16d. This was then once again discarded into the fourth well 16d. Next, 100 ul of the fifth reagent was then aspirated 114 from the cuvette 16g, held 117 for 2 minutes, and then transferred back to the cuvette 16g and mixed 114. The sample was then read 116 at 660 nm as described herein elsewhere.

This procedure was repeated for six different concentrations of hs-CRP.

Data is shown in the table below:

| hsCRP (mg/L) | OD660 |
|---|---|
| 0 | 0.0487 |
| 0.35 | 0.1377 |
| 1.46 | 0.5504 |
| 4.25 | 1.068 |
| 9.74 | 1.7413 |
| 17.97 | 2.2135 |

This data is visually illustrated in FIG. 19.

Example—IGF-1 Results Illustrated in FIG. 20

Assay cartridge and cuvette preparation included preparation of pipette tips according to a modified method as discussed above. This coating procedure was substantially similar to that described above, excepting that the procedure now was performed with capture anti insulin-like growth factor 1 (anti-IGF-1) antibodies.

Specifically, during the preparation 150 of pipette tips 20, capture anti-IGF-1 antibodies were bound to the inside of pipette tips 20 otherwise capable of holding 300 ul volume of solution. Initially, 100 uL of antibody solution having 5 ug/mL capture antibody in KPL buffer was aspirated and held for 30 minutes. The portion that did not bind to the side walls was then discarded. Next, 200 uL of 10 mM PBS and 0.05% Tw-20 was aspirated into the pipette tips, a portion of this bound to the side walls of the pipette tips. The portion that did not bind to the side walls was then discarded. Finally, 200 uL of 10 mM PBS, 0.05% Tw-20, 0.1% BSA was aspirated into the pipette tips and incubated for 10 minutes forming a third layer along the sidewalls of the pipette tips. The portion that did not bind to the side walls was then discarded.

Cartridges were prepared according to the above methods by dispensing the following amounts into the indicated wells:

| Well | Reagents/Components |
|---|---|
| 1 (16a) | Pipette tip with capture anti-IGF antibodies |
| 2 (16b) | [initially empty] 5 uL of sample |
| 3 (16c) | First Reagent Mixture: 200 uL 10 mM PBS, 0.05% polysorbate-type nonionic surfactant, 0.1% Bis (trimethylsilyl)acetamide (BSA) |
| 4 (16d) | Second Reagent Mixture: 380 uL 10 mM PBS, 0.05% polysorbate-type nonionic surfactant |
| 5 (16e) | Third Reagent Mixture: 130 uL anti IGF-1 antibody-HRP (100 ng/ml) in 10 mM PBS, 0.05% polysorbate-type nonionic surfactant, 0.1% Bis (trimethylsilyl)acetamide (BSA) |
| 6 (16f) | Fourth Reagent Mixture: 130 uL 10 mM PBS, 0.05% polysorbate-type nonionic surfactant |
| Cuvette (16g) | Fifth Reagent Mixture: 300 uL 3,3',5,5'-tetramethylbenzidine |

After preparation of the cartridges, the testing samples were obtained 104 and placed into the capillary sampler 18. After the analyzer identifies the selected bioassay, the cartridge is loaded into the analyzer, and the automated process 110 begins. Specifically, the analyzer employs a pipette arm and express gravity to transfer the reagents or blood sample 112 according to the specified automated process 110.

In this exemplary bioassay, the automated steps include adding 112, mixing 114, measuring 116, incubating 117, correcting 118, and reporting 119 the results to the user or other designated individual thereafter. This series of assays were initiated by transferring 150 ul of the first reagent amount from the third well 16c into the second well 16b.

Next, 8 ul of a sample with IGF-1 was then expressed 112 from the capillary sampler 18 into the second well 16b. The pipette tip with the antibodies from the first well 16a was then used to aspirate 100 uL of sample from the second well 16b. This sample was then held 117 inside the pipette tip for five minutes and then discarded back into the second well 16b.

A first wash was then performed in which 130 uL of the fourth reagent from the sixth well 16f was then aspirated and then discarded back again. A second wash was then performed with 55 uL of the second reagent from the fourth well 16d followed by a 75 uL air gap. This was then discarded into the third well 16c. This was repeated as a third wash.

Next, analyte labeling was performed by aspirating 100 uL of the third reagent from the fifth well 16e and holding 117 for 5 minutes. This was then discarded back into the fifth well 16e.

Four additional washes of the pipette tip were then performed. In the fourth wash, 130 uL of the first reagent were aspirated 114 from the third well 16c and then discarded back into the third well 16c. In the fifth wash, 65 uL of the second reagent were aspirated 114 from the fourth well 16d, followed by a 65 uL air gap. This was also then discarded into the third well 16c. In the sixth wash, 65 uL of the second reagent was aspirated 114 from the fourth well 16d, followed by a 65 uL air gap. This was also then discarded into the third well 16c. In the seventh wash, 130 uL of the second reagent was again aspirated 114 from the fourth well 16d. This was then once again discarded into the fourth well 16d. Next, 100 ul of the fifth reagent was then aspirated 114 from the cuvette 16g, held 117 for 5 minutes, and then transferred back to the cuvette 16g and mixed 114. The sample was then read 116 at 660 nm as described herein elsewhere.

This procedure was repeated for six different concentrations of IGF-1. Data is shown in the table below:

| IGF-1 (mg/L) | OD660 |
|---|---|
| 0 | 0.239 |
| 10 | 0.259 |
| 20 | 0.333 |
| 40 | 0.399 |
| 100 | 0.54 |
| 1000 | 1.086 |

This data is visually illustrated in FIG. 20.

Method of Correcting for Hemoglobin Levels—FIGS. 21 & 22

The present invention seeks to address several sources of laboratory error for optical detection related ELISA procedures. As clot formation within a sample can effect an optical absorption reading, and clot formation is dependent upon the passage of time, one of the largest sources of laboratory error for optical detection related ELISA procedures is due to the passage of time between sampling and measuring.

One of the principles of the present invention is to address the prior art's failure to address the increased number of errors which can occur due to the passage of time between sample taking and detecting (measuring). By pre-packaging the assay components in an all-inclusive cartridge and providing pre-selected components for assay methodology, the present invention expedites the pre-detecting stages.

Another way in which the present invention achieves this goal is by providing a bioassay which is capable of achieving accurate results by using whole blood samples without the need to separate the red blood cells from the plasma before testing. Currently available point-of-care analyzers require the use of blood plasma as the sample. This requires separation of the red blood cells from the plasma in a blood sample before obtaining test results and further prolongs the period of time between the sample taking and testing.

One of the reasons current analyzers require blood plasma was discovered to be due to the inability of prior art automated systems and assays to provide self-correcting analysis. Levels of hemoglobin in the blood samples will have an impact upon the optical density of a sample. The present inventors have found that failure to adjust the signal output of optical density to account for the variations in personal hemoglobin amounts can create errors in correctly identifying levels of CRP.

In order to address the errors of the prior art, with regard to this potential source of error, the present invention provides a modified ELISA bioassay method with auto-correction for hemoglobin. For the described assay embodiment using whole blood, the optical density of the sample is measured at a visible wavelength. Sequentially, the hemoglobin level is determined by measuring the sample optical density at another visible wavelength. The CRP level is then corrected using the hemoglobin measurement for the adjusted true plasma value of the sample.

In this way, the present invention fulfills another purpose: addressing the failure of the prior art methods to account for variations in a personal patients' plasma volume. Statistically, there is a direct correlation between the amount of plasma in a patient's blood sample, and the amount of hemoglobin detected. A healthy, typical human's blood may contain anywhere between 12-17 g/dL of hemoglobin. The World Health Organization reports that detected hemoglobin levels for non-anemic individuals may vary depending upon age, altitude, and sex:

6 months to 4 years: At or above 11 g/dL
5-12 years: At or above 11.5 g/dL
12-15 years: At or above 12 g/dL
Adult male: At or above 13.0 g/dL to 17.2 g/dL
Adult female: At or above 12.1 to 15.1 g/dL
During pregnancy: At or above 11 g/dL However, variations in the amounts of hemoglobin for specific patients have been recorded to exist between 8-12 g/dL, for example, in patients with anemia, or between 15.0 g/dL and 19 g/dL, for example, in patients who smoke, live in higher altitudes, or take drugs or hormones, such as erythropoietin which stimulates red blood cell production. Higher HGB levels indicate that a larger percentage of the volume of the whole blood sample is occupied by red blood cells. Lower HGB levels indicate that a smaller percentage of the volume of the whole blood sample is occupied by red blood cells.

As previously stated, the analytes being detected are carried within the patient's plasma. Practically speaking then, when using optical detection for determining analyte concentration, a higher HGB level (relative to sample size) means that there is a lower volume of plasma (relative to sample size) which is available for analysis. In prior art methods that failed to account for the variation in plasma levels, this led to results which reported values which were lower than were actually present within the patient.

Alternatively, an HGB level (relative to sample size) which was lower than normal, indicates that there was a higher volume of plasma (relative to sample size) which was available for analysis. In prior art methods that failed to account for the variation in plasma levels, this led to results which reported analyte values which were higher than were actually present within the patient.

The present inventive method facilitates the expansion of instrument capabilities to include multiple signal measuring devices such as, but not limited to, light emitting diodes (LED's) at multiple wavelengths. Measuring the optical density of the commixture to read the assay is preferably performed at a visible wavelength, in a range of 620 nm to 700 nm, more preferably between 650 to 680 nm, even more preferably between 658 nm and 668 nm, and most preferably at 660 nm. Measuring the optical density of the sample to read the hemoglobin levels is preferably performed at a visible wavelength, in a range of 500 nm and 550 nm, more preferably between 510 nm and 545 nm, even more preferably between 520 nm and 540 nm, and most preferably at 530 nm.

Tests were performed to illustrate the effect of various levels of hemoglobin (hematocrit effect) on the CRP detected, the results are graphically illustrated in FIGS. 21 and 22. As shown here, the hemoglobin ranged from 0 to 23 g/dL. As the hemoglobin is increased, the calculated CRP of prior art methods was decreased. With the additional LED in the visible range, the CRP levels determined by the present inventive method can be corrected for the hemoglobin detected. Specifically, FIG. 22 shows the corrected CRP for hemoglobin.

The table below shows the data which is graphically illustrated in FIG. 21, identifying the sample ID, hemoglobin levels, and CRP values before correction:

| Sample | HGB mg/dl | CRP |
|--------|-----------|-------|
| 1 | 8.9 | 147.3 |
| 2 | 11.5 | 135.8 |
| 3 | 13.8 | 119.4 |
| 4 | 16.1 | 114.1 |

Following below, this table shows the data which is graphically illustrated in FIG. 22, identifying the sample ID, hemoglobin levels, and CRP values after correction:

| Sample | HGB mg/dl | CRP |
|--------|-----------|-------|
| 1 | 8.9 | 117.4 |
| 2 | 11.5 | 123.1 |
| 3 | 13.8 | 118.5 |
| 4 | 16.1 | 122.3 |

In this way, the present inventors have adjusted the signal output of optical density to account for the variations in personal hemoglobin amounts to obviate errors in correctly identifying CRP values. Specifically, the present inventive method normalizes all results to HGB concentration of 14 g/dL before providing corrected CRP levels to a user.

CONCLUSION

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A disposable bioassay diagnostic cartridge for performing an enzyme-linked immunosorbent assay (ELISA) for a single patient, wherein the disposable bioassay diagnostic cartridge has a plurality of wells, the disposable bioassay diagnostic cartridge comprising:

a pipette tip with internal sidewalls disposed in a first well of the plurality of wells, the internal sidewalls being pretreated and coated with antibodies;

a reagent mixture disposed in a second well of the plurality of wells, the reagent mixture comprising at least one reagent selected from the group consisting of a pH stabilizer, an ionic catalyst control agent, an ionic intracellular inhibitory control agent, a detergent, a negative control agent, a chelating agent, a biocide preservative, an antibody, and a conjugate stabilizing agent; and at least a chromogenic substrate and a visualizing reagent disposed in an integrated cuvette of the plurality of wells.

2. The disposable bioassay diagnostic cartridge according to claim 1, wherein the antibodies coating the internal sidewalls are selected from the group consisting of anti-c-reactive protein antibodies, anti-cystatin-c antibodies, anti-insulin-like growth factor 1 (anti-IGF-1) antibodies, anti-alanine aminotransferase antibodies, and anti-aspartate aminotransferase antibodies.

3. The disposable bioassay diagnostic cartridge according to claim 1, wherein the chromogenic substrate and the antibodies are present in a ratio of approximately 1:1.

4. The disposable bioassay diagnostic cartridge according to claim 1, wherein the chromogenic substrate is 3,3',5,5'-tetramethylbenzidine.

5. The disposable bioassay diagnostic cartridge according to claim 1, wherein the at least one reagent is present in an amount corresponding to an amount of the chromogenic substrate and the visualizing reagent.

6. The disposable bioassay diagnostic cartridge according to claim 1, wherein the at least one reagent consists of at least 150 uL of a mixture of a lysing solution with 0.002% saponin, 0.01% low-foaming surfactant, and 0.02% sodium azide.

7. The disposable bioassay diagnostic cartridge according to claim 1, further comprising a third well of the plurality of wells having phosphate buffered saline (PBS), 0.05% polysorbate-type nonionic surfactant, and 0.03% biocide preservative.

8. The disposable bioassay diagnostic cartridge according to claim 1, further comprising a third well of the plurality of wells having antibodies selected from the group consisting of anti-c-reactive protein antibodies, anti-cystatin-c antibodies, anti-insulin-like growth factor 1 (anti-IGF-1) antibodies, anti-alanine aminotransferase antibodies, anti-aspartate aminotransferase antibodies, a conjugate stabilizing agent, and 0.5% antifoaming/defoaming agent.

9. The disposable bioassay diagnostic cartridge according to claim 1, wherein the antibodies coating the sidewalls of the pipette tip are anti-cystatin C antibodies and the at least one reagent in the second well consists of a lysing solution with 0.002% saponin, 0.01% low-foaming surfactant, and 0.02% sodium azide.

10. The disposable bioassay diagnostic cartridge according to claim 1, further comprising:

a third well of the plurality of wells having 10 mM phosphate buffered saline (PBS), 0.05% polysorbate-type nonionic surfactant, and 0.03% biocide preservative; and a fourth well of the plurality of wells having antibodies selected from the group consisting of anti-c-reactive protein antibodies, anti-cystatin-c antibodies, anti-insulin-like growth factor 1 (anti-IGF-1) antibodies, anti-alanine aminotransferase antibodies, anti-aspartate aminotransferase antibodies, a conjugate stabilizing agent, and 0.5% antifoaming/defoaming agent.

11. The disposable bioassay diagnostic cartridge according to claim 1, wherein the integrated cuvette has a first wall and a second wall capable of facilitating a first optical detection reading via a first light-emitting diode (LED) at 530 nm and a second optical detection reading via a second LED at 660 nm.

12. An enzyme-linked immunosorbent bioassay diagnostic kit comprising:

a fingerstick device; and a cartridge having a plurality of wells and an optical cuvette, the cartridge having a a pipette tip disposed in one of the plurality of wells and bioassay components disposed in one or more remaining wells of the plurality of wells;

wherein the pipette tip has sidewalls coated with an antibody; and wherein the bioassay components comprise at least one reagent being chosen from a group consisting of a pH stabilizer, an ionic catalyst control agent, an ionic intracellular inhibitory control agent, a detergent, a negative control agent, a chelating agent, a biocide preservative, an antibody, a conjugate stabilizing agent, a chromogenic substrate, and a visualizing reagent.

13. A method of preparing a disposable pipette for use in performing enzyme-linked immunosorbent assays while reducing washing time, the method comprising steps of:

pretreating a pipette tip by coating an internal surface of the pipette tip, wherein the pretreating step includes:

disposing a first coating containing an affinity agent along the internal surface of the pipette tip;

disposing a second coating containing a blocking solution over the first coating along the internal surface of the pipette tip; and disposing a third coating containing an activity preservative over the second coating along the internal surface of the pipette tip, forming a coated pipette tip for use in performing the enzyme-linked immunosorbent assays that reduces washing time by facilitating direct pipetting into the coated pipette tip with at least one reagent mixture being selected from the group consisting of a pH stabilizer, an ionic catalyst control agent, an ionic intracellular inhibitory control agent, a detergent, a negative control agent, a chelating agent, a biocide preservative, a first antibody, and a conjugate stabilizing agent; and providing one well containing a chromogenic substrate and a visualizing reagent within a cartridge for directly reacting the chromogenic substrate and the visualizing reagent with the affinity agent in the coated pipette tip.

14. The method according to claim 13, further comprising:

selecting the affinity agent from a group consisting of a second antibody, an antibody fragment, a recombinant protein, protein A, protein G, protein A/G, streptavidin, a recombinant protein fragment, a nucleic acid, a polysaccharide, a glycoprotein, peptidoglycan, a molecular imprinted polymer, and an aptamer molecule.

15. The method according to claim 13, further comprising:

selecting a coating buffer from a group consisting of a carbonate/bicarbonate buffer, a sucrose buffer, phosphate buffered saline, and tris (hydroxymethyl) aminomethane saline.

16. The method according to claim 13, wherein the step of disposing the first coating along the internal surface of the pipette tip with the affinity agent comprises:

selecting the affinity agent;

selecting a coating buffer;

preparing an antibody solution by mixing the selected first antibody and the selected coating buffer;

filling the pipette tip with the mixed antibody solution; and incubating the pipette tip for a predefined time.

17. The method according to claim 13, wherein the step of disposing the second coating over the first coating along the internal surface of the pipette tip with the blocking solution comprises:

selecting the blocking solution;

filling the pipette tip with the blocking solution; and incubating the pipette tip for a predefined time.

18. The method according to claim 13, wherein the step of disposing the third coating over the second coating along the internal surface of the pipette tip with the activity preservative comprises:

selecting the activity preservative;

filling the pipette tip with the activity preservative; and incubating the pipette tip for a predefined time.

\* \* \* \* \*